United States Patent
Thornton

(10) Patent No.: US 8,444,415 B2
(45) Date of Patent: May 21, 2013

(54) DENTAL MEASUREMENT APPARATUS AND SYSTEM

(75) Inventor: W. Keith Thornton, Dallas, TX (US)

(73) Assignee: AirWay Technologies, LLC, Carrollton, TX (US)

( * ) Notice: Subject to any disclaimer, the term of this patent is extended or adjusted under 35 U.S.C. 154(b) by 5 days.

(21) Appl. No.: 12/892,253

(22) Filed: Sep. 28, 2010

(65) Prior Publication Data

US 2011/0091834 A1    Apr. 21, 2011

Related U.S. Application Data

(60) Provisional application No. 61/252,306, filed on Oct. 16, 2009.

(51) Int. Cl.
*A61C 19/04* (2006.01)
*A61C 3/00* (2006.01)

(52) U.S. Cl.
USPC .......................................... 433/68; 433/215

(58) Field of Classification Search
USPC ............... 433/68, 69, 72, 75, 42, 50, 63, 140, 433/214, 215, 229; 33/513, 514; 600/237, 600/239, 590; 73/1.79, 1.81
See application file for complete search history.

(56) References Cited

U.S. PATENT DOCUMENTS

| | | | |
|---|---|---|---|
| 4,026,024 A | 5/1977 | Tradowsky | |
| 4,168,574 A * | 9/1979 | Chase | 33/567.1 |
| 4,439,147 A | 3/1984 | Magill et al. | |
| 4,602,905 A | 7/1986 | O'Keefe, III | |
| 4,639,220 A | 1/1987 | Nara et al. | |
| 4,715,368 A | 12/1987 | George | |
| 4,834,112 A * | 5/1989 | Machek et al. | 600/587 |
| 4,932,867 A | 6/1990 | Ueno | |
| 4,938,230 A * | 7/1990 | Machek et al. | 600/590 |
| RE33,442 E | 11/1990 | George | |
| 5,028,232 A | 7/1991 | Snow | |
| 5,078,600 A | 1/1992 | Austin | |
| 5,097,820 A * | 3/1992 | Shulman et al. | 600/237 |
| 5,154,609 A | 10/1992 | George | |
| 5,176,516 A * | 1/1993 | Koizumi | 433/72 |
| 5,678,567 A | 10/1997 | Thornton et al. | |
| 6,105,269 A * | 8/2000 | Kondrat | 33/512 |
| 6,430,830 B1 * | 8/2002 | Segal | 33/513 |

* cited by examiner

*Primary Examiner* — Cris L Rodriguez
*Assistant Examiner* — Matthew Seward
(74) *Attorney, Agent, or Firm* — Baker Botts L.L.P.

(57) ABSTRACT

An apparatus for measuring mandibular position is disclosed. In one embodiment, the apparatus includes a first slide operable to adjustably couple to a second slide, such that the second slide is operable to travel in a direction substantially parallel to a long axis of the first slide, and an indicator configured to indicate a location of the second slide relative to the first slide in the direction substantially parallel to the long axis of the first slide. The apparatus further includes an adjustment mechanism coupled to the first slide and the second slide, the adjustment mechanism configured to adjust the distance between the first slide and the second slide in a direction substantially orthogonal to the long axis of the first slide.

31 Claims, 14 Drawing Sheets

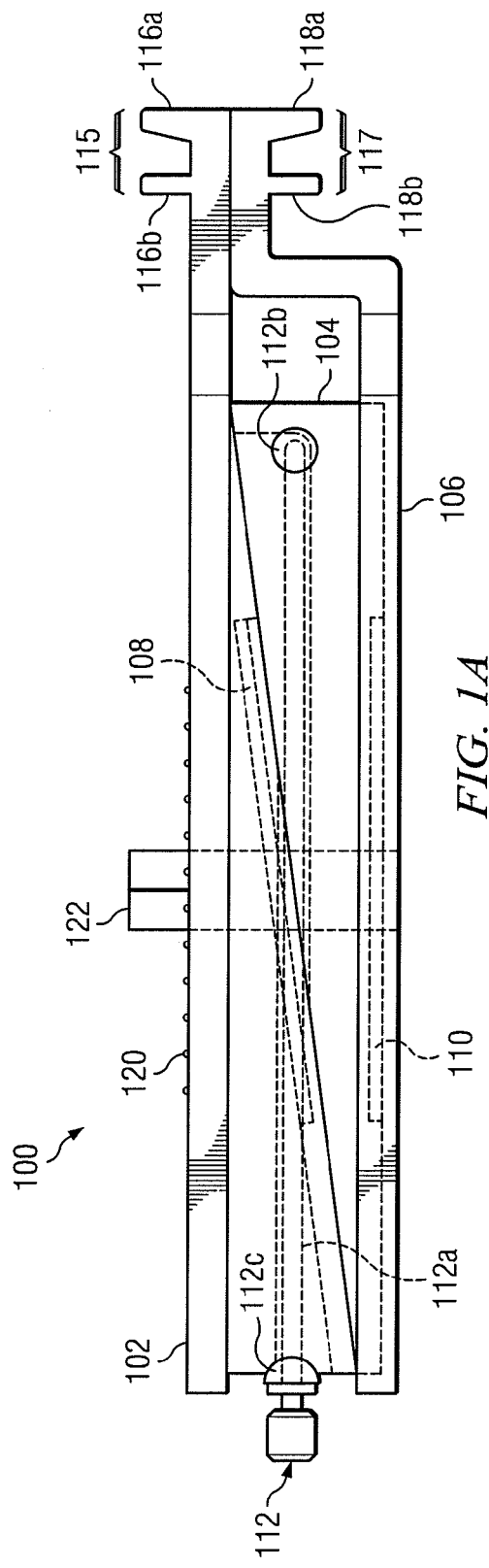
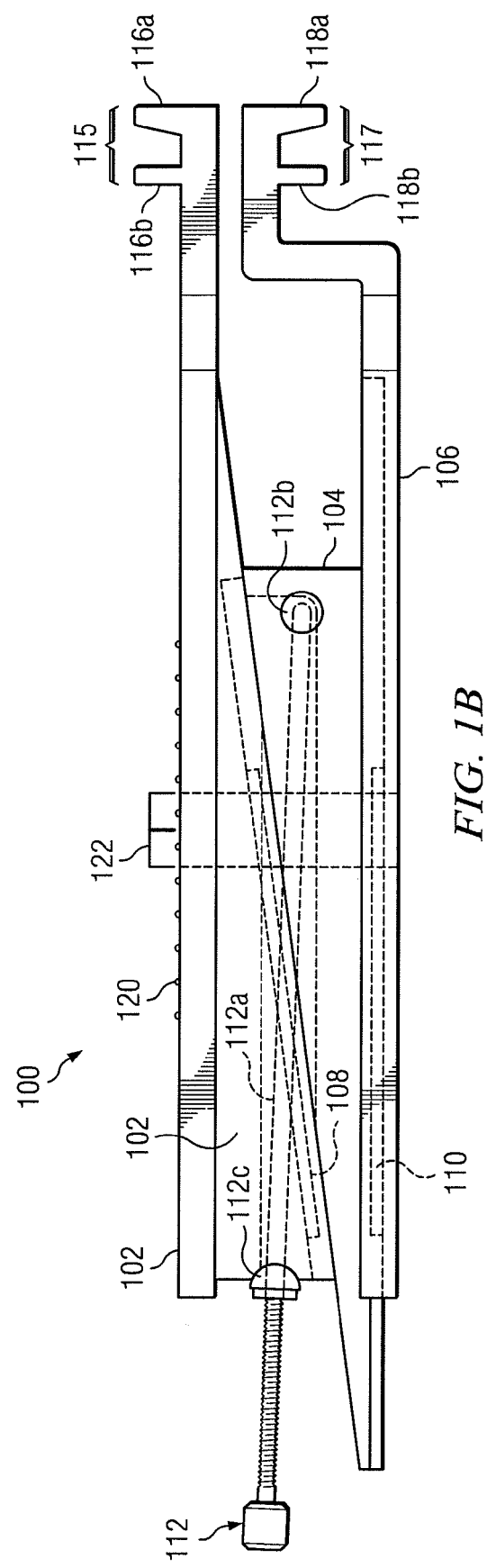
FIG. 1A
FIG. 1B

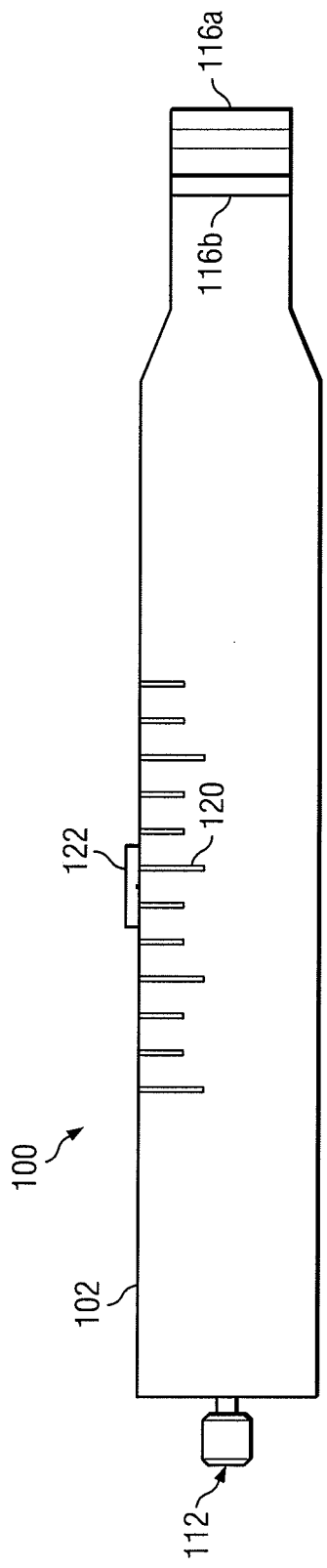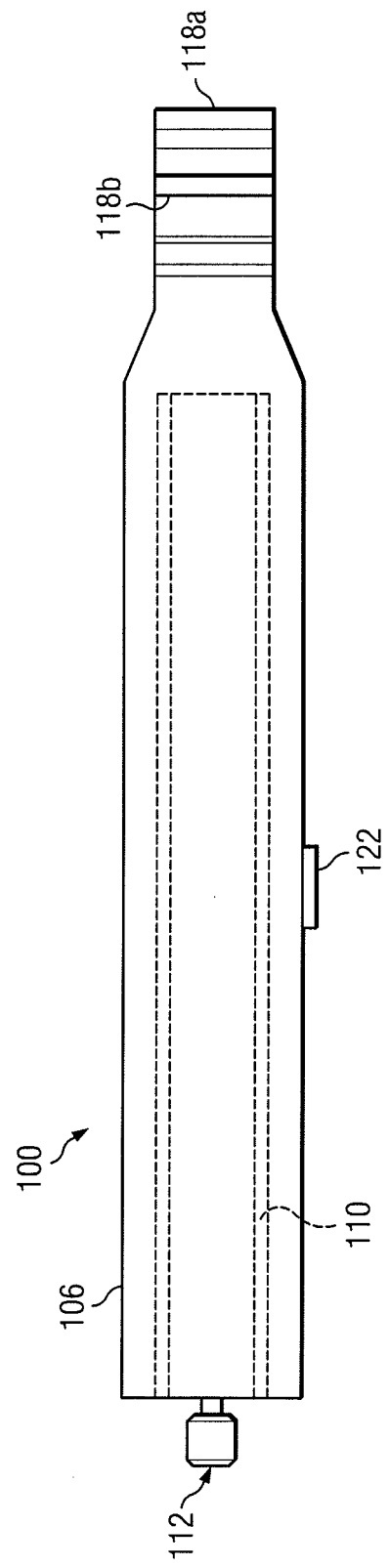
FIG. 3A
FIG. 3B

DENTAL MEASUREMENT APPARATUS AND SYSTEM

RELATED APPLICATION

This application claims priority to U.S. Provisional Application No. 61/252,306 filed Oct. 16, 2009.

TECHNICAL FIELD OF THE INVENTION

This disclosure relates generally to dental apparatuses, and more particularly to dental measurement apparatuses and systems for measuring mandibular position.

BACKGROUND OF THE INVENTION

When custom-fitting oral appliances, practitioners often take measurements of a patient's dental arch, mouth, and jaw. One particular measurement is the position of a user's mandible as he or she extends the mandible in an anterior or posterior direction. Measuring the mandibular position allows a practitioner to custom-fit oral appliances designed to extend a user's jaw forward.

OVERVIEW

In accordance with one embodiment of the present disclosure, an apparatus for measuring mandibular position comprises a first slide operable to adjustably couple to a second slide, such that the second slide is operable to travel in a direction substantially parallel to a long axis of the first slide. The apparatus further comprises an indicator configured to indicate a location of the second slide relative to the first slide in the direction substantially parallel to the long axis of the first slide. Additionally, the apparatus comprises an adjustment mechanism coupled to the first slide and the second slide, the adjustment mechanism configured to adjust the distance between the first slide and the second slide in a direction substantially orthogonal to the long axis of the first slide.

In accordance with another embodiment of the present disclosure, an apparatus for measuring mandibular position comprises a middle slide, an upper slide, and a lower slide. The middle slide comprises a tapered portion and a planar portion, wherein the middle slide is configured to adjustably couple to an upper slide and adjustably couple to a lower slide. The upper slide comprises a proximal end configured to be positioned proximate to the dentition of a user, a distal end configured to be positioned remote from the dentition of a user, and a tapered portion configured to adjustably couple to the middle slide and travel along the tapered portion of the middle slide. The upper slide further comprises an upper projection coupled to the proximal end of the upper slide, wherein the upper projection is configured to engage with at least a portion of a user's maxillary dentition. The lower slide comprises a proximal end configured to be positioned proximate to the mandibular dentition of the user, and wherein the lower slide is configured to adjustably couple to the middle slide. The lower slide further comprises a lower projection coupled to the proximal end of the lower slide, wherein the lower projection is configured to engage with at least a portion of the user's mandibular dentition. The apparatus further comprises an indicator configured to indicate a location of the lower slide relative to the upper slide in a direction substantially parallel to a long axis of the first slide and an adjustment mechanism configured to adjust a distance between the upper slide and the lower slide in a direction substantially orthogonal to the long axis of the upper slide.

In accordance with yet another embodiment of the present disclosure, a system for measuring mandibular position comprises a first slide and a second slide configured to adjustably couple to the first slide. The system further comprises an indicator operable to indicate a location of the second slide relative to the first slide in a direction substantially parallel to a long axis of the first slide. Additionally, the system comprises a plurality of inserts configured to couple to the second slide, wherein each of the inserts has a projection height in a direction orthogonal to the long axis of the first slide, and wherein the projection height is different for each of the plurality of inserts.

In accordance with yet another embodiment of the present disclosure, a system for measuring mandibular position comprises a first slide comprising a proximal end configured to be positioned proximate to an anterior side of a user and a plurality of second slides. Each of the second slides is configured to removably couple to the first slide and travel in a direction substantially parallel to a long axis of the first slide. Additionally, each of plurality of the second slides comprises a bite portion configured to be positioned proximate to an anterior side of the user, wherein each of the bite portions comprises a bite portion height in a direction orthogonal to a long axis of the second slide, and wherein the bite portion height is different for each of the plurality of second slides. The system further comprises an indicator configured to indicate a location of one of the plurality of second slides relative to the first slide in a direction substantially parallel to the long axis of the first slide.

Technical advantages of certain aspects of the present disclosure include the ability to measure a user's mandibular position at varying angles of mandibular opening. For example, particular embodiments of the present disclosure allow a dental practitioner to take measurements of a user's mandibular position across varying angles of mandibular opening using a single adjustable apparatus. As a result, a practitioner does not need more than one device to measure a mandibular position across varying angles of mandibular opening. Other particular embodiments of the present disclosure include the ability to take measurements of a user's mandibular position across varying angles of mandibular opening using one or more interchangeable components. As a result, a practitioner may customize the angle of mandibular opening at which the mandibular position is measured by utilizing interchangeable components of varying thicknesses or sizes. Thus, a practitioner can customize particular measurements without having to replace an entire measurement system. Accordingly, a practitioner may use such measurements to properly align and/or size an oral appliance for use by the user. Other technical advantages of the present disclosure will be readily apparent to one skilled in the art from the following figures, description, and claims. Moreover, while specific advantages have been enumerated above, various embodiments may include all, some, or none of the enumerated advantages.

BRIEF DESCRIPTION OF THE DRAWINGS

For a more complete understanding of the present disclosure and at least some of its advantages, reference is now made to the following description taken in conjunction with the accompanying drawings, in which:

FIG. 1A illustrates an example embodiment of an apparatus for measuring mandibular position;

FIG. 1B illustrates an alternative view of the example embodiment of the apparatus illustrated in FIG. 1A;

FIG. 3A illustrates a perspective view of the example embodiment of the apparatus illustrated in FIGS. 1A and 1B;

FIG. 3B illustrates an alternative perspective view of the example embodiment of the apparatus illustrated in FIGS. 1A and 1B;

DETAILED DESCRIPTION

Figure 2:
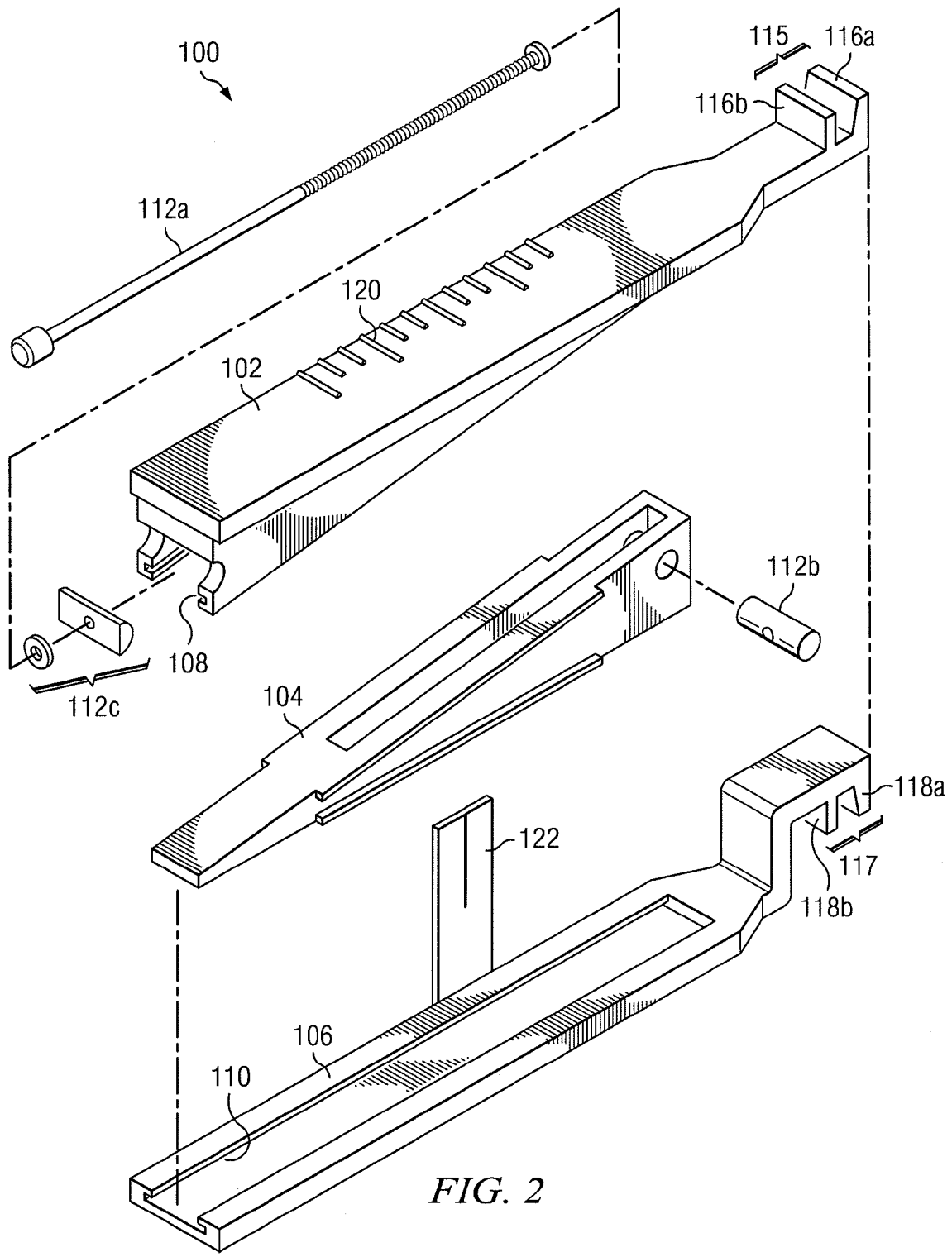
FIG. 2 illustrates an exploded view of the example apparatus illustrated in FIGS. 1A and 1B.

FIGS. 1A and 1B illustrate a particular embodiment of an adjustable dental measurement device 100 for measuring a user's mandibular position. In general, device 100 may be used to measure a user's mandibular position across varying angles of mandibular opening. Device 100 may include upper slide 102, middle slide 104, lower slide 106, upper guide 108, lower guide 110, adjustment mechanism 112, upper bite portion 115, upper projections 116a and 116b, lower bite portion 117, lower projections 118a and 118b, measurement scale 120, and indicator 122. In operation, upper bite portion 115 and lower bite portion 117 may be positioned on a user's maxillary dentition and a user's mandibular dentition. The user's mandible may be extended in an anterior direction, causing indicator 122 to move along measurement scale 120. The extent of the user's mandibular position may then be measured. The process may be repeated to determine a user's mandibular position across varying angles of mandibular opening. Such measurements may enable a dental practitioner to properly align and/or size an oral appliance for use by the user. In particular embodiments, device 100 may include one or more interchangeable upper projections 116a and 116b, lower projections 118a and 118b, and/or lower slides 106 of varying sizes that enable a user's mandibular position to be measured as the mandible is extended in an anterior or forward direction at varying angles of mandibular opening. As discussed further below, FIG. 1A illustrates device 100 in a "base" position and FIG. 1B illustrates device 100 in an "adjusted" position. For purposes of this description, a "base" position may represent a configuration of device 100 in which upper slide 102 and lower slide 106 are at a minimum height. An "adjusted" position may represent a configuration of device 100 in which device 100 has been adjusted so that a height between upper slide 102 and lower slide 106 is increased relative to the base position. For purposes of this description, a "height" between upper slide 102 and lower slide 106 may represent a distance in a direction orthogonal to a long axis of upper slide 102 and lower slide 106.

Upper slide 102 includes upper projections 116a and 116b and upper guide 108, and engages with middle slide 104 in upper guide 108. Upper slide 102 may include a proximal end and a distal end. For purposes of this description, the proximal end of upper slide 102 may represent an end or extremity of device 100 proximate to the dentition of a user when device 100 is in operation. The distal end of upper slide 102 may represent an end or extremity of device 100 that is remote to the dentition of a user when device 100 is in operation. In particular embodiments, upper slide 102 may comprise a tapered lower surface and a planar upper surface. The tapered lower surface of upper slide 102 may cooperate with a tapered surface of middle slide 104 to adjust a relative height between upper slide 102 and lower slide 106. Additionally, upper guide 108 may be integrally formed with or coupled to upper slide 102. In particular embodiments, upper slide 102 may include upper bite portion 115 on the proximal end of upper slide 102, which may engage a user's maxillary dentition by placing at least a portion of a user's maxillary dentition on, adjacent to, or between upper projections 116a and 116b. In conjunction with upper projections 116a and 116b, upper bite portion 115 provides a bite surface for a user, and locates upper slide 102 in the user's mouth. In particular embodiments, upper slide 102 includes an appropriately sized inner bore that aligns with an inner bore of middle slide 104 and accommodates adjustment mechanism 112. Additionally, upper slide 102 may include measurement scale 120, which may be marked, indicated, or otherwise denoted on an upper surface of upper slide 102. Upper slide 102 may be made from any appropriate material suitable to perform the described functions. In particular embodiments, upper slide 102 may be constructed of a biocompatible metal, polymer, or plastic.

Middle slide 104 couples to upper slide 102 by coupling to upper guide 108, and couples to lower slide 106 by coupling to lower guide 110. Middle slide 104 may comprise a proximal end and a distal end. Similar to upper slide 102, a proximal end of middle slide 104 may represent an end or extremity of device 100 proximate to the dentition of a user when device 100 is in operation. The distal end of middle slide 104 may represent an end or extremity of device 100 that is remote to the dentition of a user when device 100 is in operation. In particular embodiments, middle slide 104 may couple to upper slide 102 by sliding or fitting within a groove of upper guide 108, and may couple to lower slide 106 by sliding or fitting within a groove of lower guide 110. Additionally, middle slide 104 may include a tapered upper surface and a planar lower surface. In particular embodiments, middle slide 104 includes an appropriately sized inner bore that accommodates adjustment mechanism 112. Additionally, middle slide 104 may cooperate with adjustment mechanism 112 and upper slide 102 to adjust a distance between upper slide 102 and lower slide 102. For example, the tapered upper surface of middle slide 104 may be configured to move along a cooperatively shaped tapered lower surface of upper slide 102. As middle slide 104 moves along the tapered lower surface of upper slide 102, the tapered upper surface of middle slide 104 operates as a "wedge," driving upper slide 102 and lower slide 106 apart. As noted above, the height between upper slide 102 and lower slide 106 may represent a distance in a direction orthogonal to a long axis of upper slide 102 and lower slide 106. As discussed further below, middle slide 104 may move along the tapered upper surface of upper slide 102 as adjustment mechanism 112 receives a rotational force.

Lower slide 106 includes lower projections 118a and 118b and lower guide 110, and receives middle slide 104 in lower guide 110. Lower slide 106 may comprise a proximal end and a distal end. Similar to upper slide 102 and middle slide 104, the proximal end of lower slide 106 may represent an end or extremity of device 100 proximate to the dentition of a user when device 100 is in operation. The distal end of lower slide 106 may represent an end or extremity of device 100 that is remote to the dentition of a user when device 100 is in operation. As shown in FIG. 1, lower slide 106 may comprise a planar upper surface in parallel with a planar lower surface. Lower slide 106 may engage with middle slide 104 in lower guide 110, positioned along a planar upper surface of lower slide 106. Additionally, lower slide 106 may comprise lower bite portion 117 which may engage with a user's mandibular dentition by placing at least a portion of a user's mandibular dentition on, adjacent to, or between lower projections 118a and 118b. In conjunction with lower projections 118a and 118b, lower bite portion 117 provides a bite surface for a user, and locates lower slide 106 in the user's mouth. Lower slide 106 may additionally include or couple to indicator 122, and may indicate a mandibular position by moving indicator 122 along a side portion of upper slide 102 proximate to measurement scale 120. Lower slide 106 may be made from any appropriate material suitable to perform the described functions. In particular embodiments, lower slide 106 may be constructed of a biocompatible metal, polymer, or plastic.

Upper guide 108 represents one or more grooves or slots attached to upper slide 102 along which middle slide 104 travels. In particular embodiments, upper guide 108 may be attached to a tapered lower surface of upper slide 102, or may be integrally formed with upper slide 102. Upper guide 108 may be appropriately sized so that upper slide 102 resists loose movement of middle slide 104, yet guides the movement of middle slide 104 along upper guide 108. In general upper guide 108 may be any device or mechanism suitable to engage with middle slide 104 to guide the movement of middle slide 104.

Lower guide 110 represents one or more grooves or slots coupled to middle slide 104 along which lower slide 106 moves. In particular embodiments, lower guide 110 may be attached to a planar lower surface of middle slide 104, or may be integrally formed with a planar lower surface of middle slide 104. Lower guide 110 may be appropriately sized so that middle slide 104 resists loose movement of lower slide 106, yet guides the movement of lower slide 106 along lower guide 110. In general, however, lower guide 110 may be any device or mechanism suitable to engage middle slide 104 and to guide the movement of middle slide 104.

Adjustment mechanism 112 adjusts a distance between upper slide 102 and lower slide 104 in a direction orthogonal to a long axis of upper slide 102 and lower slide 106. In particular embodiments, adjustment mechanism may include adjustment screw 112a, pivot pin 112b, and adjustment nut 112c. In such embodiments, adjustment screw 112a may be coupled to pivot pin 112b at the proximal end of middle slide 104 and to adjustment nut 112c at the distal end of upper slide 102. Additionally, adjustment screw 112a, in conjunction with adjustment nut 112c, translates rotational force applied to adjustment screw 112a to linear force that causes middle slide 104 to travel along upper guide 108. Additionally, adjustment screw 112a may couple to middle slide 104 at pivot pin 112b to allow adjustment screw 112a to freely pivot at the point of attachment to middle slide 104. As shown in FIG. 1B, this may provide adjustment screw 112a with the flexibility to change angles as middle slide 104 moves relative to upper slide 102. In general, however, adjustment mechanism may represent any mechanism or device suitable to adjust the distance or height between upper slide 102 and lower slide 106.

Upper projections 116a and 116b may couple to upper slide 102 and may engage with a user's maxillary dentition. In particular embodiments, upper projections 116a and 116b may each be coupled to upper bite portion 115 on the proximal end of upper slide 102. For example, in particular embodiments, different sets of upper projections 116 may be interchanged and utilized in different configurations of device 100 to further adjust a relative height between upper slide 102 and lower slide 106 as discussed below with respect to FIG. 6. In other particular embodiments, as in the example embodiment shown in FIG. 1, upper projections 116a and 116b may be integrally formed with upper slide 102. In general, however, upper projections 116a and 116b may comprise any appropriate shape or form suitable to perform the described functions.

Lower projections 118a and 118b may be coupled to lower slide 106 and may engage a user's mandibular dentition. In particular embodiments, lower projections 118a and 118b may each couple to lower bite portion 117 on a proximal end of lower slide 106. As shown in FIG. 1, lower projections 118a and 118b may be integrally formed with upper slide 102. As described above with respect to upper projections 116a and 116b, in other particular embodiments, lower projections 118a and 118b may be removably coupled to lower slide 106. Accordingly, a practitioner may utilize different sets of lower projections 118a and 118b for different configurations of device 100 to further adjust a relative height between upper slide 102 and lower slide 106.

Measurement scale 120 represents any index or series of numbers or markings suitable to indicate a mandibular position of a user. In particular embodiments, measurement scale may include notches, lines, numbers, or any other appropriate markings suitable to measure mandibular position. Although measurement scale 120 depicts measurements in centimeters, for purposes of example, measurement scale 120 may represent a scale in millimeters, inches, fractions of an inch, or any other appropriate scale or index. Additionally, measurement scale 120 may include bidirectional measurements. For example, device 100 may be able to indicate the user's mandibular position as the user moves the mandible in an anterior or posterior direction. In such embodiments, measurement scale 120 may include measurements extending in both directions from a center or index point of zero. Measurement scale 120 may additionally be adjustable along a long axis of upper slide 102, thereby enabling a practitioner or user to calibrate measurement scale 120.

Indicator 122 may extend above an upper planar surface of upper slide 102 and may indicate a location of lower slide 106 relative to upper slide 102 to indicate a user's mandibular position. In particular embodiments, indicator 122 may be coupled to or integrally formed with lower slide 106, and may move along a side portion of upper slide 102 as lower slide 106 moves along lower guide 110. Indicator 122 may include an arrow, triangle, line, and/or any other appropriate marking or symbol suitable to indicate the user's mandibular position on measurement scale 120.

In operation, the respective proximal ends of upper slide 102 and lower slide 106 engage with a user's maxillary and mandibular dentition. Upper slide 102 and lower slide 106 may be positioned on a user's maxillary and mandibular dentition by a user, a medical practitioner, or other person. In particular embodiments, at least a portion of a user's maxillary dentition may be placed on upper bite portion 115 and at least a portion of a user's mandibular dentition may be placed on lower bite portion 117. For example, at least a portion of a user's maxillary dentition may be placed between upper projections 116a and 116, and at least a portion of a user's mandibular dentition may be placed between upper projections 118a and 118b.

Once properly engaged, the mandible may be moved into a measuring position. In particular embodiments, the measuring position may be in a forward or anterior direction, or in a rearward or posterior direction. In particular embodiments, a user may exert pressure on lower projections 118a and/or 118b to move his or her mandible into a measuring position. In other particular embodiments, a practitioner may pull on a component of device 100 to move the mandible into a measuring position. As the mandible is moved into a measuring position, lower slide 106 moves within lower guide 110, which may concurrently move indicator 122. As discussed above, indicator 122 may move along a side portion of a long axis of upper slide 102. Once the mandible is moved into a measuring position the mandibular position may be observed, recorded or otherwise determined by viewing where indicator 122 aligns with measurement scale 120. For example, indicator 122 may point to or align with the "0.5 centimeter" marking on measurement scale 120. This indicates that the mandible has moved in an anterior direction five tenths of a centimeter, or five millimeters.

In particular embodiments, one or more measurements of a user's mandibular position may be taken by measuring a mandibular position as the mandible is opened at varying angles. Thus, operation may proceed with device 100 being adjusted for different angles of mandibular opening. For example, rotational force may be applied to adjustment mechanism 112. In particular embodiments, adjustment mechanism 112 may include adjustment screw 112a coupled to pivot pin 112b on a proximal end of middle slide 104, and may cooperate with adjustment nut 112c to translate rotational force applied to adjustment screw 112 to linear motion of middle slide 104. Thus, by applying rotational force to adjustment mechanism 112, middle slide 104 may be moved relative to upper slide 102. Accordingly, middle slide 104 may operate as a "wedge," causing upper slide 102 and lower slide 106 to move further apart. As a result, turning adjustment mechanism 112 may adjust the distance between upper slide 102 and lower slide 106, and consequently, of the distance a user is required to open his or her mandible to position the user's dentition on upper bite portion 115 and lower bite portion 117. Additionally, adjustment mechanism 112 may be turned in an opposite direction to cause upper slide 102 and lower slide 106 to move closer together, decreasing the distance between upper slide 102 and lower slide 106.

Once adjusted, lower slide 106 may be adjusted so that indicator 122 aligns with a "0" indicator on measurement scale 120, thus calibrating device 100. Device 100 may be repositioned on a user's maxillary and mandibular dentition being placed at least a portion of a user's maxillary dentition on upper bite portion 115 of upper slide 102 and at least a portion of a user's mandibular dentition on lower bite portion 117 of lower slide 106. The mandible may then be extended into a measuring position. As discussed above, as the mandible is extended into a measuring position, lower slide 106 moves along lower guide 110. In particular embodiments, lower slide 106 may concurrently move indicator 122. Indicator 122 may move along a side portion of a long axis of upper slide 102 in proximity to measurement scale 120. Once the mandible is extended in an anterior direction to a desired extent, the user's mandibular position as device 100 is in an adjusted position may be observed, recorded, or otherwise determined by viewing where indicator 122 aligns with measurement scale 120.

The above-described process may be repeated and/or supplemented with any appropriate number of measurements. In particular, adjustment mechanism 112 may be used to adjust device 100 to several positions of varying distance between upper slide 102 and lower slide 106, enabling the mandibular position to be measured across varying angles of mandibular opening. The number of measurements taken, and the corresponding number of times, and to what degree, device 100 is adjusted may be configured according the particular needs of a user, medical practitioner or other person.

FIG. 2 is an exploded view of device 100 as illustrated in FIG. 1. As discussed above, device 100 illustrated in FIG. 2 includes upper slide 102, middle slide 104, lower slide 106, upper guide 108, lower guide 110, adjustment mechanism 112 (including adjustment screw 112a, pivot pin 112b, and adjustment nut 112c), upper bite portion 115, upper projections 116a and 116b, lower bite portion 117, lower projections 118a and 118b, measurement scale 120, and indicator 122. When assembled, lower slide 106 moves along lower guide 110 as a user's mandible is moved into a measuring position. As lower slide moves along lower guide 110, lower slide 106 causes indicator 122 to indicate a location of lower slide 106 relative to upper slide 102.

FIGS. 3A-3D illustrate various perspective views of an example embodiment of device 100 as described in FIG. 1. As discussed above with respect to FIG. 1, the example embodiment of device 100 illustrated in FIGS. 3A-3D includes upper slide 102, middle slide 104, lower slide 106, upper guide 108, lower guide 110, adjustment mechanism 112, upper bite portion 115, upper projections 116a and 116b, lower bite portion 117, lower projections 118a and 118b, measurement scale 120, and indicator 122.

FIG. 3A illustrates a top view of an example embodiment of device 100. As shown in FIG. 3A, device 100 includes an upper slide 102, upper bite portion 115, upper projections 116a and 116b, adjustment mechanism 112, measurement scale 120, and indicator 122. Components of device 100 not shown in FIG. 3A include lower slide 106, upper guide 108, lower guide 110, lower bite portion and lower projections 118a and 118b.

FIG. 3B illustrates a bottom view of an example embodiment of device 100. As shown in FIG. 3B, device 100 includes middle slide 104, lower slide 106, lower guide 110, adjustment mechanism 112, lower bite portion 117, and lower projections 118a and 118b. Components of device 100 not shown in FIG. 3B include upper slide 102, upper projections 116a and 116b, measurement scale 120, and indicator 122.

Figure 3C:
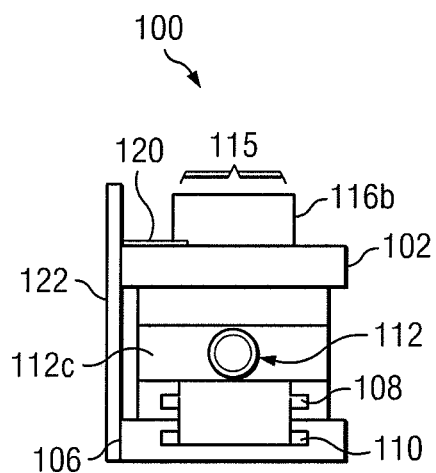
FIG. 3C illustrates another alternative perspective view of the example embodiment of the apparatus illustrated in FIGS. 1A and 1B.

FIG. 3C illustrates a frontal view of an example embodiment of device 100. For purposes of this example, the frontal view represents a view looking at the distal end of device 100. As shown in FIG. 3C, device 100 includes upper slide 102, middle slide 104, lower slide 106, upper guide 108, adjustment mechanism 112, upper bite portion 115, upper projections 116a and 116b, lower bite portion 117, lower projections 118a and 118b, and indicator 122. Components of device 100 not shown in FIG. 3C include measurement scale 120.

Figure 3D:
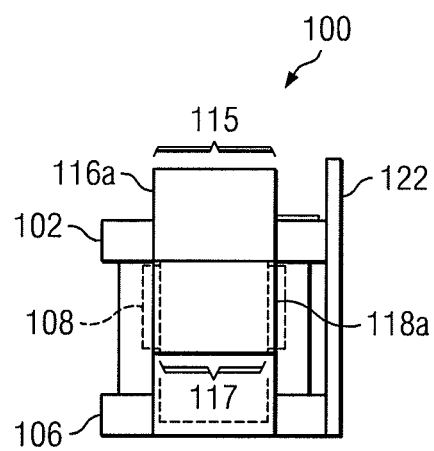
FIG. 3D illustrates yet another alternative perspective view of the example embodiment of the apparatus illustrated in FIGS. 1A and 1B.

FIG. 3D illustrates a rear view of an example embodiment of device 100. For purposes of this example, the rear view of device 100 represents a view looking at the proximal end of device 100. As shown in FIG. 3D, device 100 includes upper slide 102, lower slide 106, upper guide 108, upper bite portion 115, upper projections 116a and 116b, lower bite portion 117, lower projections 118a and 118b, and indicator 122. Components of device 100 not shown in FIG. 3D include adjustment mechanism 112, and measurement scale 120.

Figure 4A:
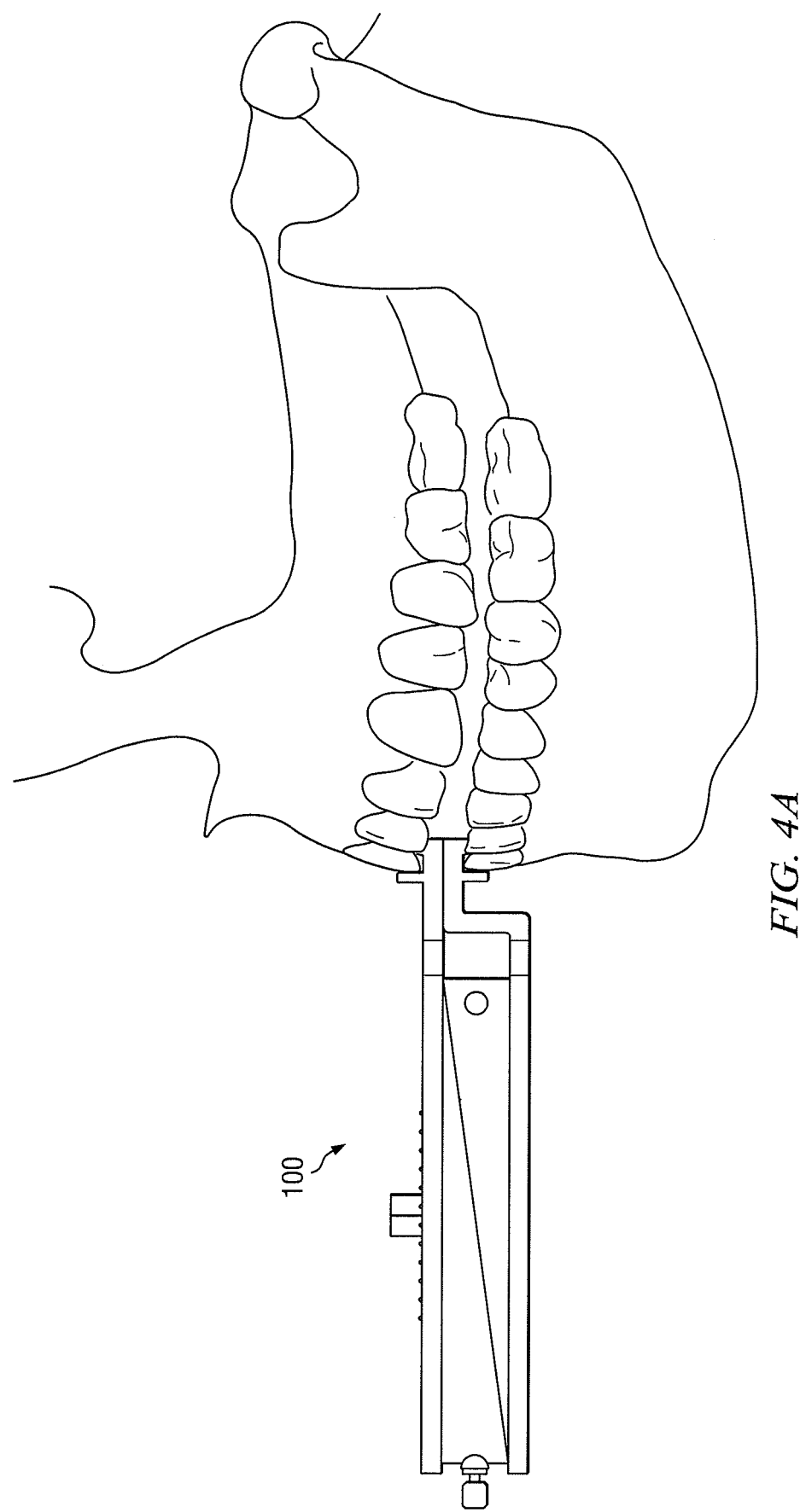
FIG. 4A illustrates a view of an example embodiment of the apparatus illustrated in FIGS. 1A and 1B as positioned to measure mandibular position.
Figure 4B:
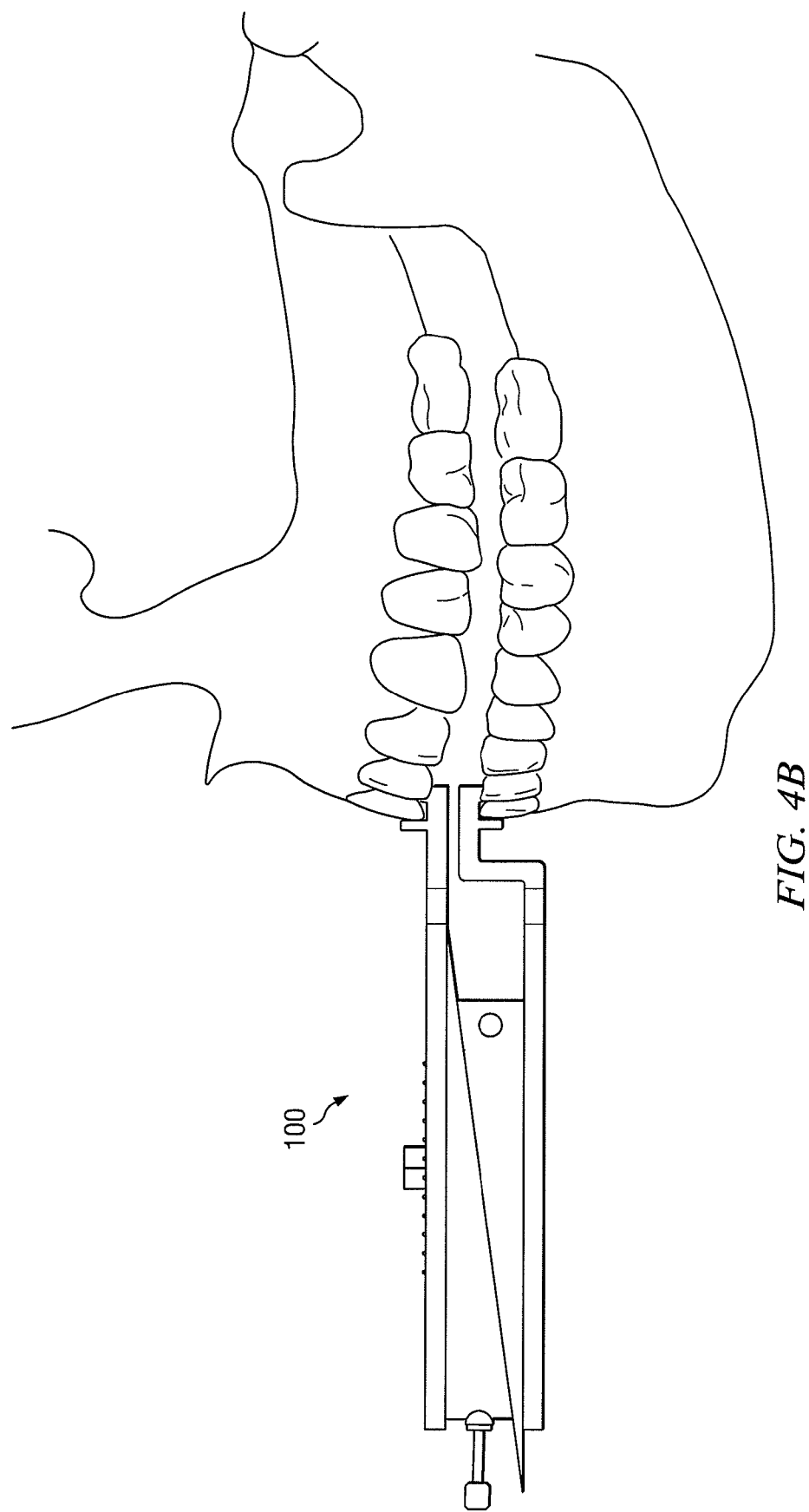
FIG. 4B illustrates a view of an example embodiment of the apparatus illustrated in FIGS. 1A and 1B as positioned to measure mandibular position.
Figure 4C:
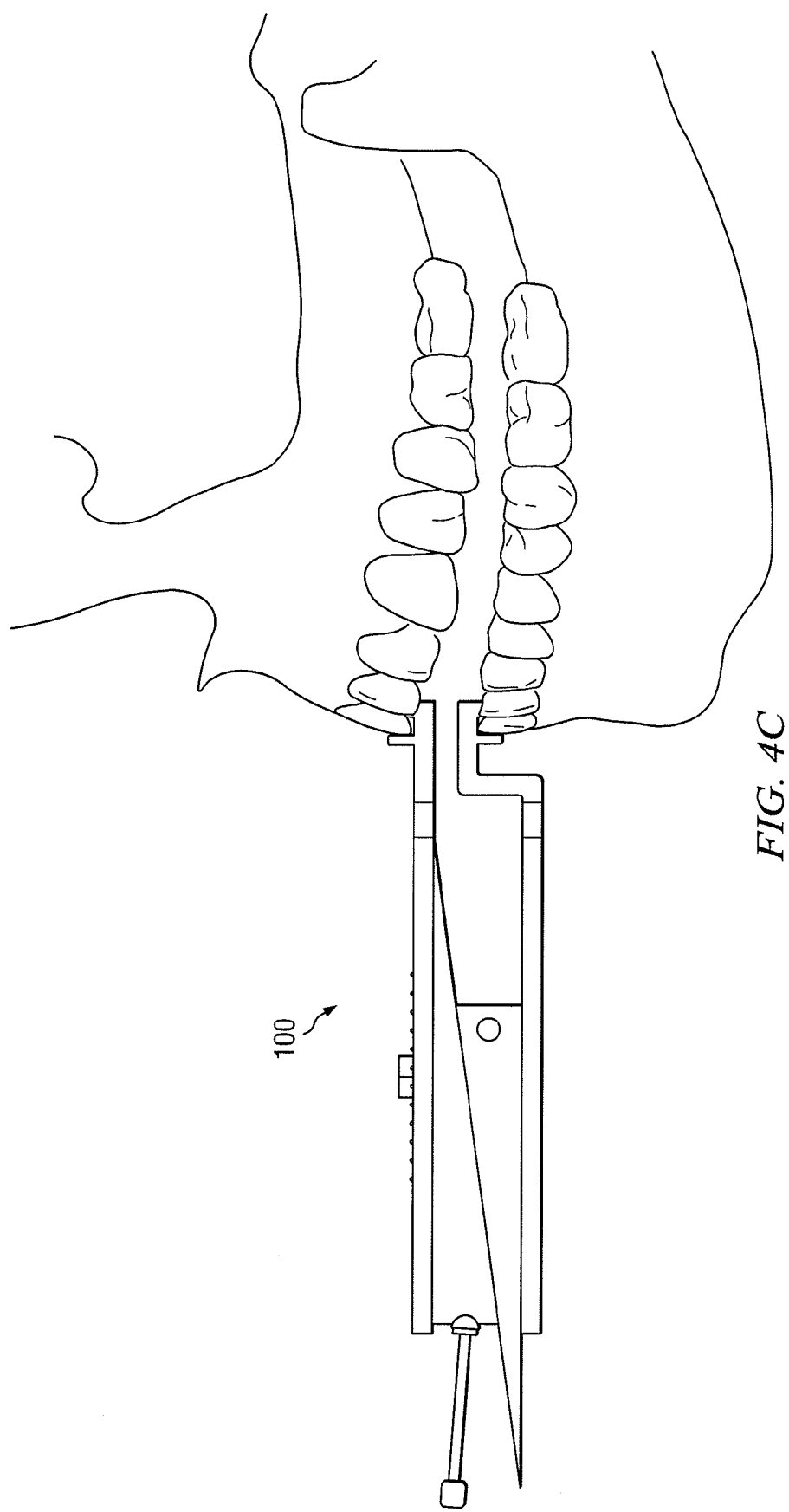
FIG. 4C illustrates a view of an example embodiment of the apparatus illustrated in FIGS. 1A and 1B as positioned to measure mandibular position.

FIGS. 4A-4C illustrate an example embodiment of device 100 illustrated in FIG. 1 as implemented on a user, with device 100 adjusted to fit different angles of mandibular opening. FIG. 4A illustrates an embodiment of device 100 as positioned on a user's maxillary and mandibular dentition with device 100 configured in a base, or minimum-height position. FIG. 4B illustrates an embodiment of device 100 as positioned on a user's maxillary and mandibular dentition with device 100 configured in an adjusted height position. FIG. 4C illustrates an embodiment of device 100 as positioned on a user's maxillary and mandibular dentition with device 100 configured in an adjusted, maximum height position.

Figure 5:
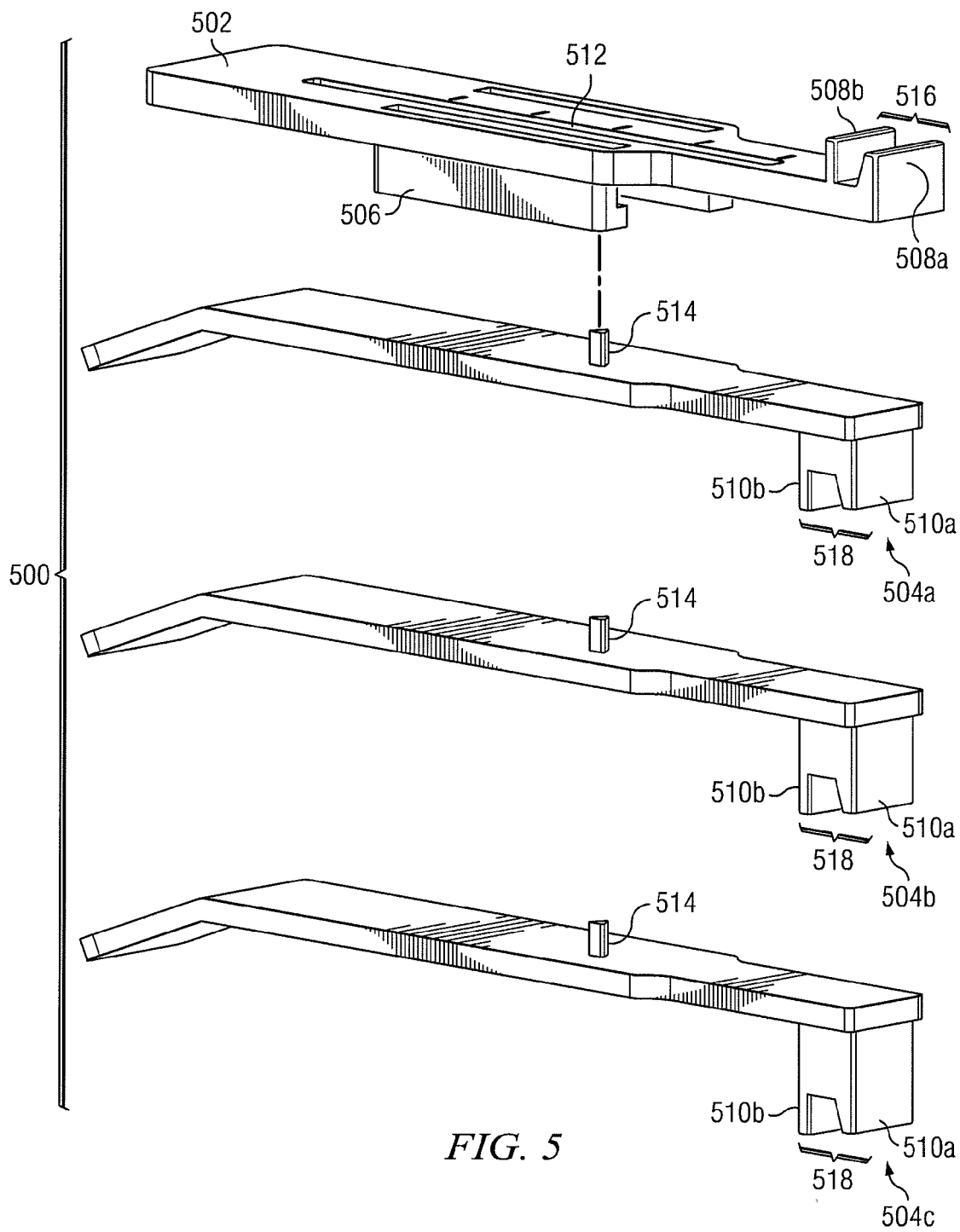
FIG. 5 illustrates an example embodiment of a system for measuring mandibular position.

FIG. 5 illustrates an example embodiment of an adjustable dental measurement system 500 including multiple components for measuring a user's mandibular position across varying angles of mandibular opening. As shown in FIG. 5, system 500 includes upper slide 502, lower slides 504a, 504b, and 504c, upper guide 506, upper projections 508a and 508b, lower projections 510a and 510b, measurement scale 512, and indicator 514. Upper slide 502 and lower slides 504 may include upper bite portion 516 and lower bite portions 518 respectively.

As shown in FIG. 5, upper slide 502 includes upper guide 506, upper projections 508a and 508b, and upper bite portion 516. In particular embodiments, upper guide 506 may be coupled to or integrally formed with upper slide 502 on a lower surface of upper slide 502. Additionally, upper slide 502 may couple to lower slides 504 by engaging a particular lower slide 504 with upper guide 506. As shown in FIG. 5, upper bite portion 516 represents a portion or region of upper slide 502 proximate to the dentition of a user when system 500 is in operation. Additionally, upper slide 502 may engage with a user's maxillary dentition by engaging at least a portion of a user's maxillary dentition on or adjacent to upper bite portion 516. Additionally, although an upper bite portion 516 is illustrated with a particular thickness for purposes of example, upper bite portion 516 may be of any appropriate thickness in a direction orthogonal to a long axis of upper slide 502. Different thicknesses of upper bite portion 518 may be appropriate for different mandibular openings. Furthermore, as shown in FIG. 5, upper projections 508a and 508b may be integrally formed with upper bite portion 516. In other particular embodiments, upper projections 508a and 508b may each separately or jointly couple to and decouple from upper slide 502. Additionally, upper bite portion 516 may be of any appropriate size or thickness suitable to receive a portion of a user's maxillary dentition. Upper slide 502 also includes measurement scale 512, which may be marked, indicated, or otherwise denoted on an upper surface of upper slide 502. In particular embodiments, upper slide 502 may additionally include a slot extending along at least a portion of the long axis of upper slide 502. In particular embodiments, the slot may receive or accommodate indicator 514.

Lower slides 504a, 504b, and 504c (which may be collectively referred to as "lower slides 504" or individually as "lower slide 504") may each be configured to couple to and decouple from upper slide 502 by engaging upper guide 506. Lower slides 504 may move along upper guide 506 in response to a user's mandible being moved into a measuring position, thereby indicating a position on measurement scale 512. As shown in FIG. 5, lower slide 504 may include a lower bite portion 518 on a proximal end of lower slide 506. In particular embodiments, lower bite portion 516 may represent a portion or region of lower slide 504 proximate to the dentition of a user when system 500 is in operation. Additionally, lower slide 504 may engage a user's mandibular dentition by engaging at least a portion of a user's mandibular dentition on or adjacent to lower bite portion 518. As shown in FIG. 5, lower projections 510a and 510b may couple to or integrally form with lower bite portion 518. Additionally, as shown in FIG. 5, each of lower slides 504a, 504b, and 504c, may include a lower bite portion 518 of different thicknesses in a direction orthogonal to a long axis of lower slide 504. Different thicknesses of lower bite portion 518 may be appropriate for different angles of mandibular opening. As a result, a practitioner or user may use a different lower slide 504 to measure a user's mandibular position at different angles of mandibular opening. For example, a relatively thin lower bite portion 518 on lower slide 504a may be appropriate to measure mandibular position for a narrow mandibular opening. A mid-thickness lower bite portion 518 on lower slide 504b may be appropriate to measure mandibular position for a wider mandibular opening. A maximum-thickness lower bite portion 518 on lower slide 504c may be appropriate to measure mandibular position for a widest mandibular opening. Thus, a practitioner may measure a user's mandibular position as the mandible is extended in an anterior or posterior direction across a range of mandibular openings. Lower slides 504 may be made from any appropriate material suitable to perform the described functions. In particular embodiments, lower slides 504 may be constructed of a biocompatible metal, polymer, or plastic. Additionally, although shown for purposes of example a system 500 that includes three lower slides 504, other particular embodiments of system 500 may include any appropriate number of lower slides 504, each including any appropriate respective thicknesses of lower bite portion 518.

Upper guide 506 represents one or more grooves or slots attached to upper slide 502 along which lower slides 504a, 504b, and 504c may travel. In particular embodiments, upper guide 506 may be coupled to or integrally formed with a lower surface of upper slide 502. Upper guide 506 may be configured such that upper slide 502 resists loose movement of lower slide 504, yet guides the movement of lower slide 504 when force is applied to lower slide 504. In general, upper guide 506 may be any device or mechanism suitable to engage lower slide 504 and to guide the movement of lower slide 504.

Upper projections 508a and 508b may couple to upper slide 502 and engage with a user's maxillary dentition. In particular embodiments, upper projections 508a and 508b may be coupled to upper bite portion 516 on a proximal end of upper slide 502. Each of upper projections 508a and 508b may be integrated with upper slide 502, or may be removably coupled to upper slide 502. In particular embodiments, at least a portion of a user's maxillary dentition may be received on, adjacent to, or between a space between upper projections 508a and 508b. In general, however, system 500 may include any appropriate size or shape of upper projections 508a and 508b suitable to perform the described functions.

Lower projections 510a and 510b may couple to each of lower slides 504, and engage with at least a portion of a user's mandibular dentition. As discussed above, lower projections 510a and 510b may couple to lower bite portion 518 on a proximal end of a particular lower slide 504. Lower projections 510a and 510b may be integrally formed with a particular lower slide 504, or may be removably coupled to a particular lower slide 504. As with upper projections 508a and 508b, lower slide 504 may be placed on at least a portion of a user's mandibular dentition on, adjacent to, or between lower projections 510a and 510b. In general, system 500 may include lower projections 510a and 510b of any appropriate size or shape suitable to perform the described functions.

Measurement scale 512 represents any index or series of numbers suitable to indicate a mandibular position. In particular embodiments, measurement scale may include notches, lines, numbers, or any other appropriate markings suitable to measure a user's mandibular position. Although in the example illustrated, measurement scale 512 depicts measurements in centimeters, measurement scale 512 may depict measurements in millimeters, inches, fractions of an inch, or any other appropriate scale. Additionally, measurement scale 512 may include bidirectional measurements. For example, system 500 may be able to measure the extent of user's mandibular position in an anterior or posterior direction. In such embodiments, measurement scale 512 may include measurements extending in both directions from a center or index point of zero. Measurement scale 512 may additionally be adjustable along a long axis of upper slide 502, thereby enabling a practitioner or user to calibrate measurement scale 512 relative to lower slide 504 and indicator 514.

Indicator 514 may be coupled to lower slide 504 and, in particular embodiments, may move along a slot in the surface of upper slide 502 as lower slide 504 travels along upper guide 506. In other particular embodiments, indicator 514 may move along a side portion of upper slide 502 in proximity to measurement scale 512. Indicator 514 may represent an arrow, triangle, line, and/or any other appropriate marking or symbol positioned in any appropriate manner suitable to indicate a user's mandibular position on measurement scale 512.

With respect to the particular embodiment of system 500 illustrated in FIG. 5, operation proceeds in a similar manner to the embodiment illustrated in FIG. 1. To begin, a first slide and a plurality of second slides are accessed. In particular embodiments, the first slide may be upper slide 502 and the plurality of second slides may be lower slides 504. In particular embodiments, one of lower slides 504a, 504b, and 504c may be selected and coupled to upper slide 502 by engaging lower slide 504 with upper guide 506. For example, it may be desired to measure a user's mandibular position when the mandible is narrowly opened. Thus, lower slide 504a may be selected and coupled to upper slide 502. In general, one or more lower slides 504 may be selected and coupled to upper slide 502, by a medical practitioner, user or other person. Additionally, a user's mandibular position may be measured by a medical practitioner, user, or other person.

Once lower slide 504a is coupled to upper slide 502, upper bite portion 516 of upper slide 502 may be positioned on a user's maxillary dentition and lower bite portion 518 of lower slide 504a may be positioned on a user's mandibular dentition. Once engaged, the mandible may be moved in an anterior or forward measuring position or into a posterior or rearward direction. As the mandible is moved into a measuring position, lower slide 504a may move indicator 514. As discussed above, indicator 514 may move within a slot on the surface of upper slide 502, or may move along a side portion of upper slide 502. Once the mandible is extended in an anterior or posterior direction, the user's mandibular position may be determined by viewing a location of indicator 514 relative to measurement scale 512.

Lower slide 504a may be decoupled from upper slide 502, and a second lower slide 504 may be selected. For example, lower slide 504b may be selected and coupled to upper slide 502 to measure the user's mandibular position at a wider angle of mandibular opening. Once lower slide 504b is coupled to upper slide 502, upper bite portion 516 of upper slide 502 may be positioned on a user's maxillary dentition and lower bite portion 518 of lower slide 504b may be positioned on a user's mandibular dentition. Once in position, the mandible may be positioned in an anterior or posterior measuring position. The user's mandibular position may then be determined by observing a location of indicator 514 relative to measurement scale 512. In a similar way, lower slide 504b may then be replaced with lower slide 504c and a measurement taken with the user's mandible opened in a widest position.

The above-described process may be repeated and/or supplemented with any appropriate number of measurements. Although FIG. 5 shows for purposes of illustration a system 500 that includes three lower slides 504, particular embodiments of system 500 may include any appropriate number of lower slides 504, corresponding to the particular range and granularity with which the practitioner desires to take measurements.

Figure 5A:
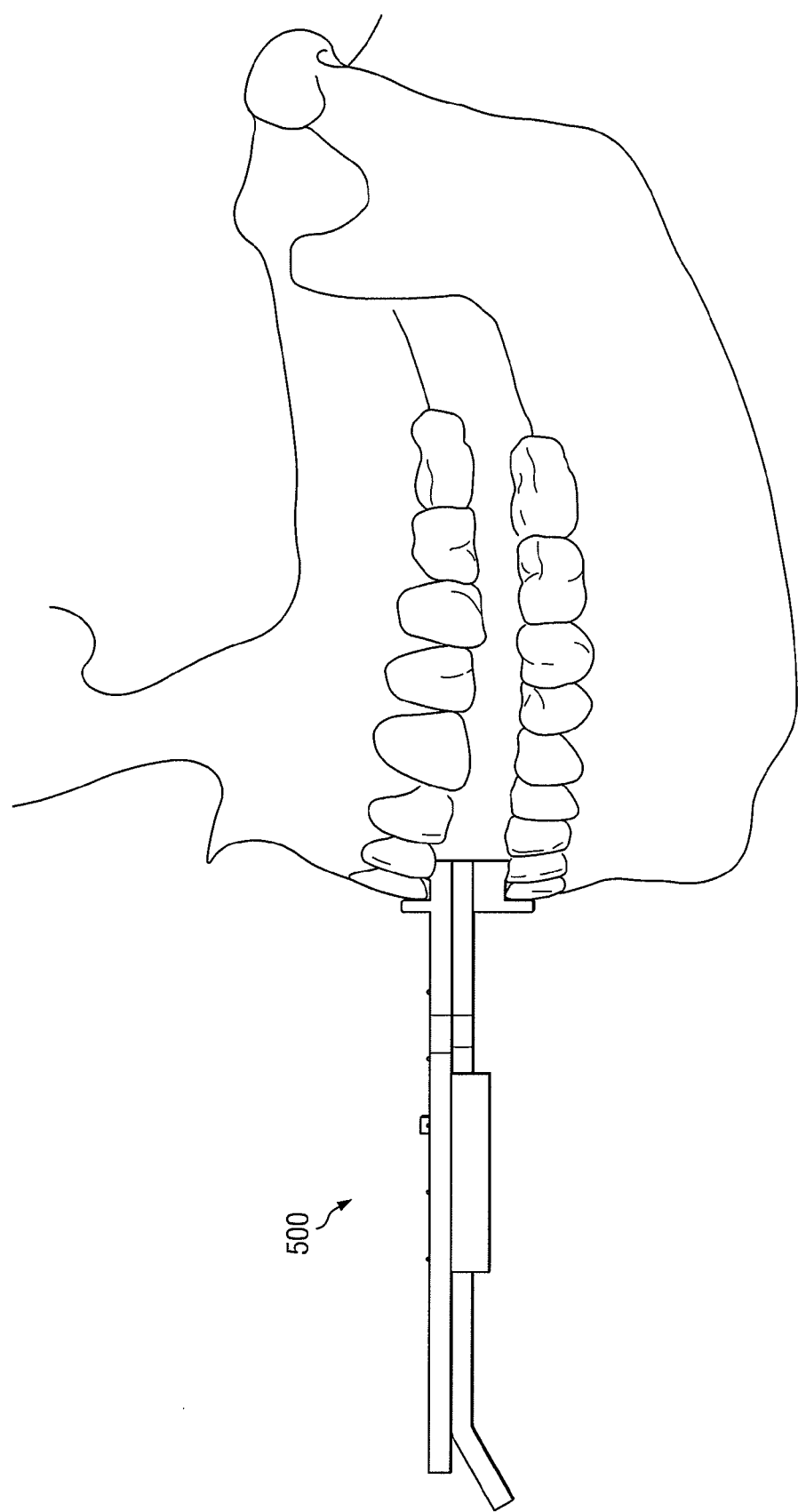
FIG. 5A illustrates a view of an example embodiment of the system illustrated in FIG. 5 as positioned on maxillary dentition and mandibular dentition.
Figure 5B:
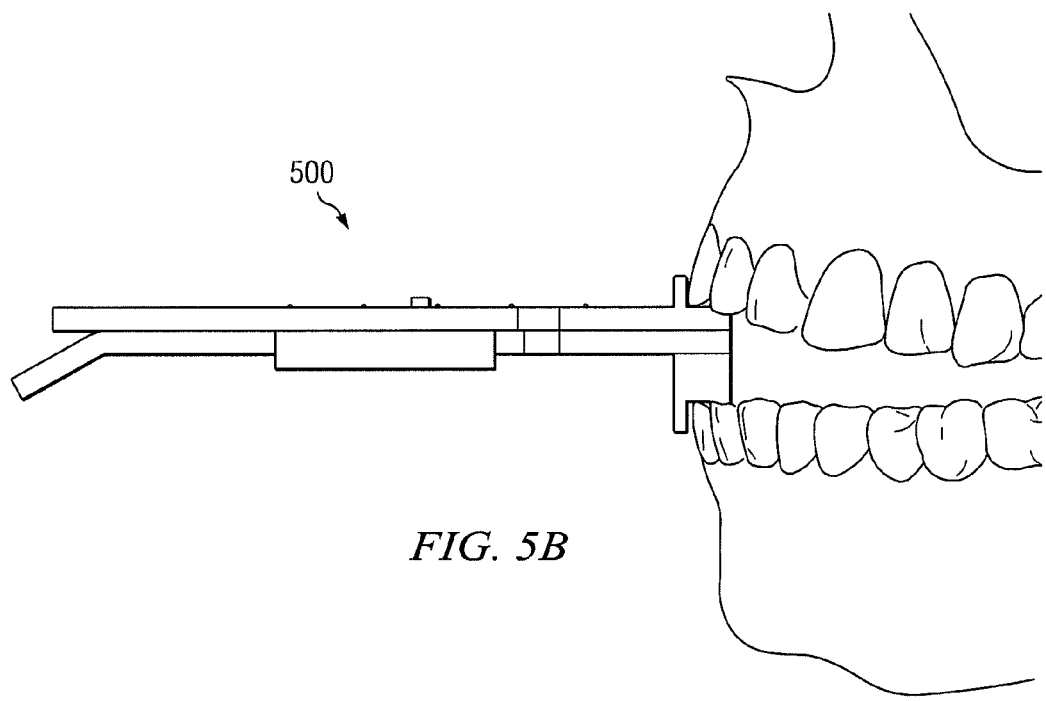
FIG. 5B illustrates an alternative view of an example embodiment of the system illustrated in FIG. 5 as positioned on maxillary dentition and mandibular dentition.
Figure 5C:
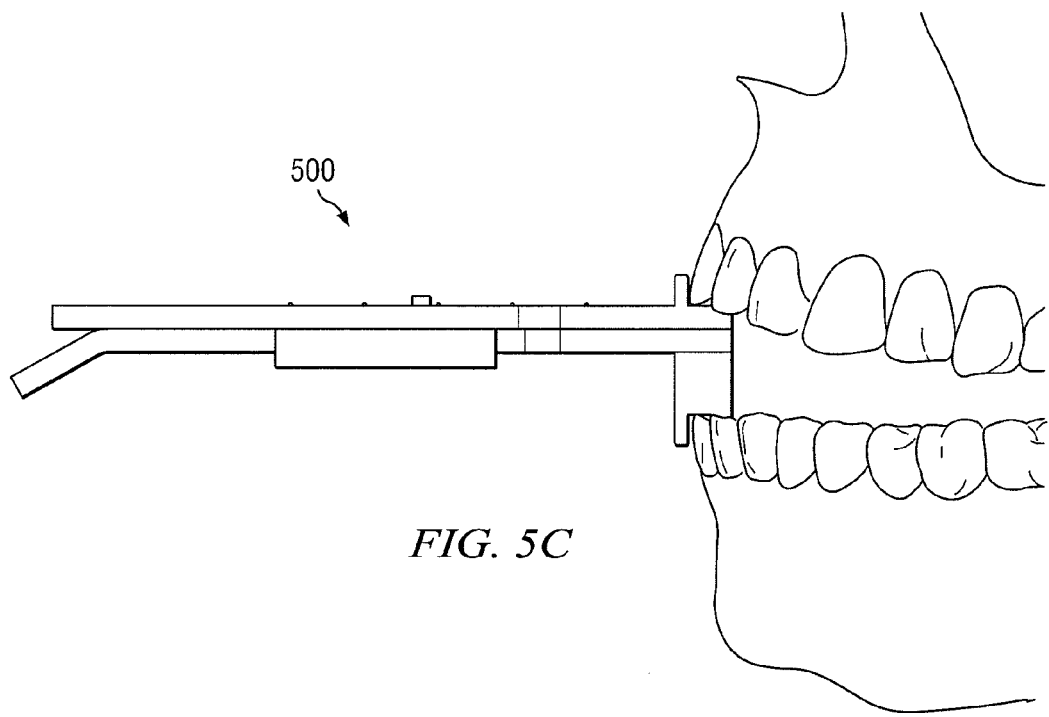
FIG. 5C illustrates another alternative view of an example embodiment of the system illustrated in FIG. 5 as positioned on maxillary dentition and mandibular dentition.

FIGS. 5A-5C illustrate an example embodiment of system 500 illustrated in FIG. 5 as implemented on a user, with system 500 adjusted to measure mandibular position across different angles of mandibular opening. FIG. 5A illustrates an embodiment of system 500 as positioned on a user's maxillary and mandibular dentition with a minimum-thickness lower bite portion 518. FIG. 5B illustrates an embodiment of system 500 as positioned on a user's maxillary and mandibular dentition with a mid-thickness lower bite portion 518. FIG. 5C illustrates an embodiment of system 500 as positioned on a user's maxillary and mandibular dentition with a maximum-thickness lower bite portion 518.

Figure 6:
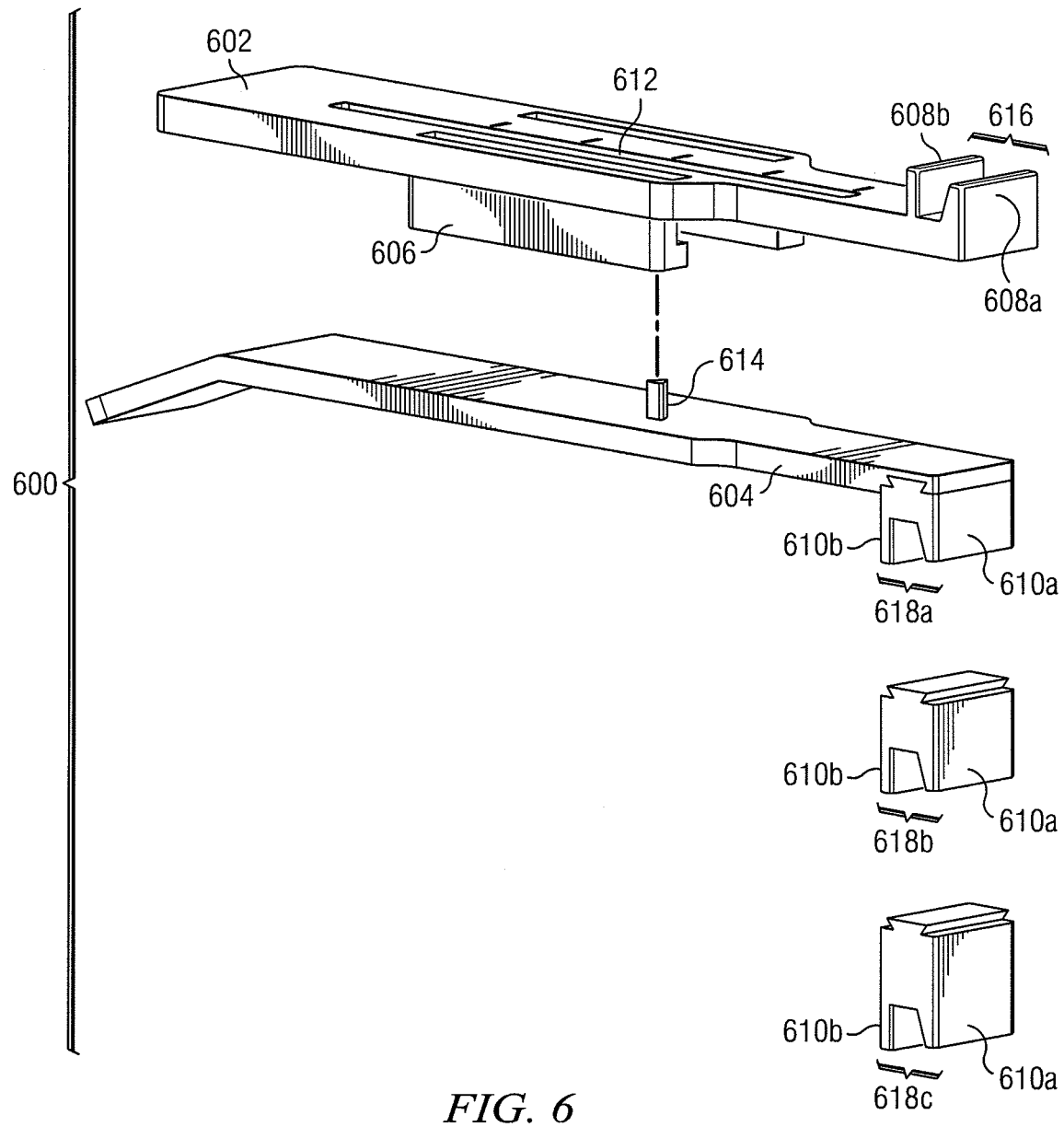
FIG. 6 illustrates another example embodiment of a system for measuring mandibular position.

FIG. 6 illustrates an example embodiment of a system 600 including multiple components. System 600 may measure a user's mandibular position across varying angles of mandibular opening. As shown in FIG. 6, system 600 includes upper slide 602, lower slide 604, upper guide 606, upper projections 608a and 608b, lower projections 610a and 610b, measurement scale 612, indicator 614, upper bite insert 616, and lower bite inserts 618a, 618b, 618c.

As shown in FIG. 6, upper slide 602 may couple to and decouple from lower slide 604. In particular embodiments, upper slide 602 may include upper guide 606 and measurement scale 612. Upper slide 602 may couple to lower slide 604 by engaging lower slide 604 with upper guide 606. Additionally, upper slide 602 may engage with a user's maxillary dentition by placing at least a portion of a user's maxillary dentition on upper bite insert 616. In particular embodiments, upper bite insert 616 may represent a portion or region of upper slide 602 that engages at least a portion of a user's maxillary dentition and is proximate to the dentition of a user when system 600 is in operation. Upper bite insert 616 may include upper projections 608a and 608b. Additionally, upper slide 602 may include measurement scale 612, which may be marked, indicated, or otherwise denoted on an upper surface of upper slide 602. Upper slide 602 may additionally include a slot extending along at least a portion of the long axis of upper slide 602. In particular embodiments, the slot may receive indicator 614 protruding from lower slide 604.

Lower slide 604 may couple to and decouple from upper slide 602 by engaging upper guide 606, and may indicate on measurement scale 612 a user's mandibular position. In particular embodiments, lower slide 604 may be operable to receive one or more lower projections 610. As shown in FIG. 6, lower slide 604 may comprise a planar upper surface in parallel with a planar lower surface. In particular embodiments, upper slide 602 may engage a user's mandibular dentition by placing at least a portion of a user's mandibular dentition on a selected one of lower bite inserts 618a, 618b, or 618c. In particular embodiments, lower bite insert 618 may represent a portion or region of lower slide 602 that engages with a user's mandibular dentition, and is proximate to the dentition of a user when system 600 is in operation. Additionally, at least a portion of a user's mandibular dentition may engage with lower slide 604 by being placed between lower projections 610a and 610b. As discussed further below, lower slide 604 travels along upper guide 606. As lower slide 604 travels along upper guide 606, indicator 614 moves, thereby indicating a position on measurement scale 612.

Upper guide 606 represents one or more grooves or slots attached to upper slide 602 along which lower slide 604 may travel. In particular embodiments, upper guide 606 may be attached to or integrally formed with a lower surface of upper slide 602. Upper guide 606 may be appropriately sized so that upper slide 602 resists loose movement of lower slide 604, yet guides the movement of lower slide 604 as a user's mandible is moved into a measuring position. In general, upper guide 606 may be any device or mechanism suitable to engage and guide the movement of lower slide 604.

Measurement scale 612, as discussed above with respect to FIG. 5, represents any index or series of numbers suitable to indicate a mandibular position of a user. Additionally, indicator 614 is coupled to lower slide 604 and may move along a slot in the surface of upper slide 602 as lower slide 604 moves along upper guide 606. Indicator 614 may represent an arrow, triangle, line, and/or any other appropriate marking or symbol suitable to indicate a location of upper slide 602 relative to lower slide 604.

Upper bite insert 616 may couple to and decouple from upper slide 602 and engage with a user's maxillary dentition. In the particular embodiment of system 600 illustrated in FIG. 6, upper bite insert is integrally formed with upper slide 602. In other embodiments, system 600 may include a plurality of upper bite inserts 616, where each particular upper bite insert 616 has different height in a direction orthogonal to a long axis of upper slide 602. Each upper bite insert 616 may couple to and decouple from upper slide 602. Upper bite insert 616 may couple to upper slide 602 in a transverse direction by using a dovetail configuration, a tongue-in-groove configuration, or any other appropriate configuration suitable to couple and decouple upper bite insert 616 to and from upper slide 602. As with lower bite insert 610, described further below, a practitioner may utilize one or more upper bite inserts 616 of different heights to measure a user's mandibular position at different angles of mandibular opening. For example, a relatively low-height upper bite insert 616 may be appropriate to measure a user's mandibular position when the mandible is slightly open. A mid-height upper bite insert 616 may be appropriate to measure a user's mandibular position when the mandible is opened in a wider position. A maximum-height upper bite insert 616 may be appropriate to measure the extent of a user's mandibular position when the mandible is opened in a widest position. Thus, a mandibular position may be measured at different angles of mandibular opening. In particular embodiments, upper bite insert 616 may include upper projections 608a and 608b that enable upper bite insert 616 to receive at least a portion of a user's maxilla in the space between upper projections 608a and 608b. Although the example system 600 shown includes a single upper bite insert 616, other particular embodiments of system 600 may include any appropriate number of upper bite inserts 616 of any appropriate height.

Lower bite inserts 618a, 618b, and 618c (each of which may be collectively referred to as "lower bite inserts 618" or individually referred to as "lower bite inserts 618") may couple to and decouple from lower slide 604 and each engage with a user's mandibular dentition. In particular embodiments, lower bite inserts 618 may couple to and decouple from a proximal end of lower slide 604. Lower bite inserts 618 may each couple to lower slide 604 in a transverse direction by using a dovetail configuration, a tongue-in-groove configuration, or any other appropriate configuration suitable to couple and decouple lower bite inserts 618 to and from lower slide 604. As discussed above with respect to upper bite insert 616, lower bite inserts 618a, 618b, and 618c may each be of different relative heights. In conjunction with upper bite inserts 616, utilizing lower bite inserts 618 of different heights may enable a user's mandibular position to be measured across varying angles of mandibular opening. In particular embodiments, lower bite inserts 618 may include lower projections 610a and 610b that enable lower bite inserts 618 to receive at least a portion of a user's maxilla in the space between lower projections 610a and 610b. Additionally, although the example system 600 shown includes three lower bite inserts 618, other particular embodiments of system 600 may include any appropriate number and size of lower bite inserts 618.

With respect to the particular embodiment of system 600 illustrated in FIG. 6, operation proceeds in a similar manner to the embodiment illustrated in FIG. 1A, 1B and FIG. 5. In general, one or more lower bite inserts 618 may be selected and coupled to lower slide 604 by a medical practitioner, a user, or other person. Additionally, a user's mandibular position may be measured by a medical practitioner, user, or other person. To begin, one of lower bite inserts 618a, 618b, and 618c may be selected and coupled to lower slide 604. In particular embodiments of system 600 that include a plurality of upper bite inserts 616, one of the plurality of upper bite inserts 616 may be selected and coupled to upper slide 602. Additionally, lower slide 604 is coupled to upper slide 602 by engaging lower slide 604 with upper guide 606. After lower bite insert 618 is coupled to lower slide 604, upper slide 602 may be positioned on a user's maxillary dentition by placing at least a portion of the user's maxillary dentition on upper bite insert 616. Additionally, lower slide 604 may be positioned on a user's mandibular dentition by placing at least a portion of the user's mandibular dentition on lower bite insert 618. Once properly engaged, a user's mandible may be positioned in an anterior or posterior direction. As the mandible is positioned, lower slide 604 may move indicator 614. Once the mandible is positioned, the user's mandibular position may be observed, recorded, or otherwise determined by viewing where indicator 614 aligns with measurement scale 612. The above-described process may be repeated by coupling lower bite inserts 618 of different sizes to lower slide 604. By selecting an appropriately-sized upper bite insert 616 and lower bite insert 618, a practitioner may measure a user's mandibular position across varying angles of mandibular opening.

Figure 6A:
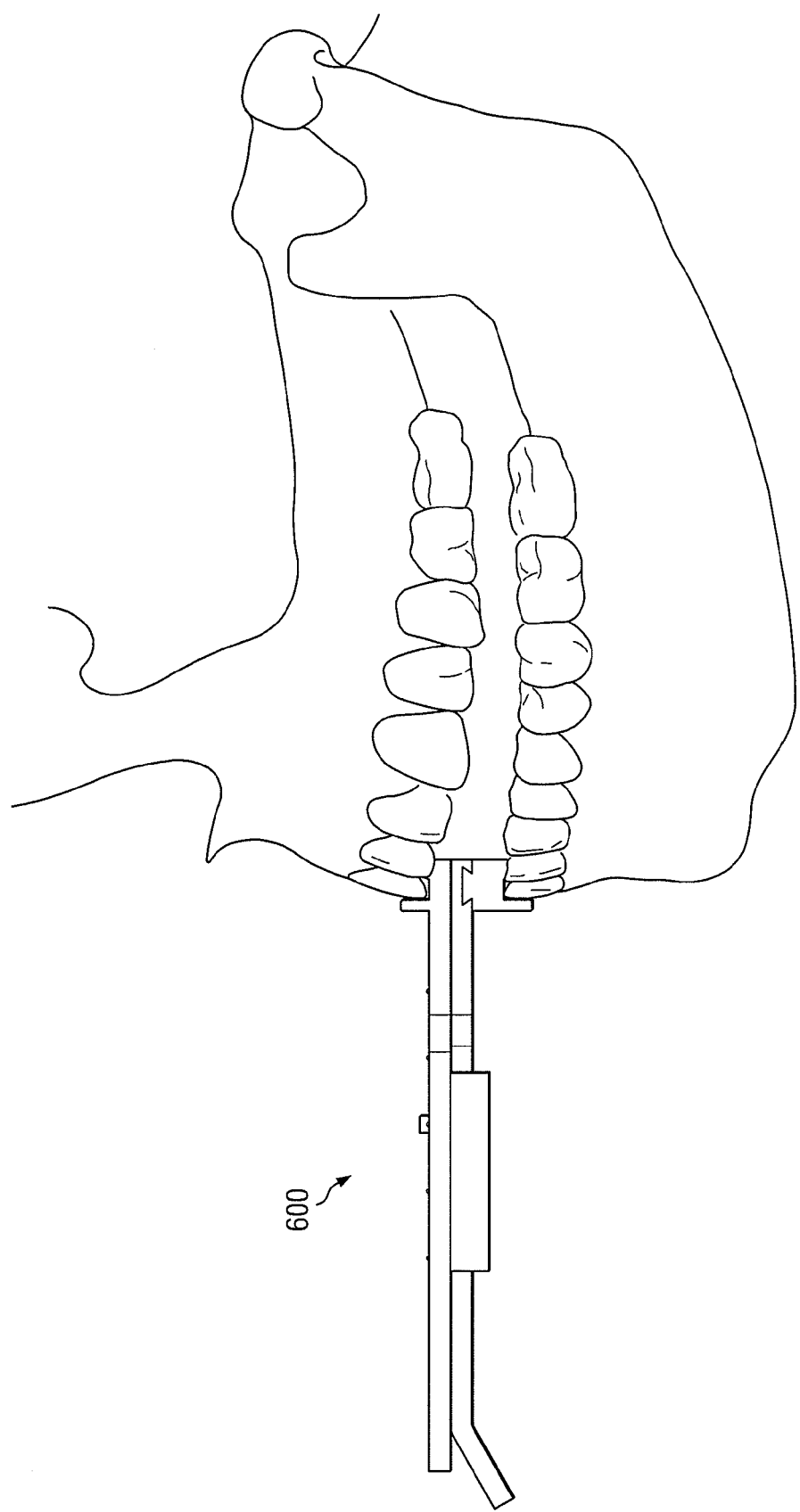
FIG. 6A illustrates a view of an example embodiment of the system illustrated in FIG. 6 as positioned on maxillary dentition and mandibular dentition.
Figure 6B:
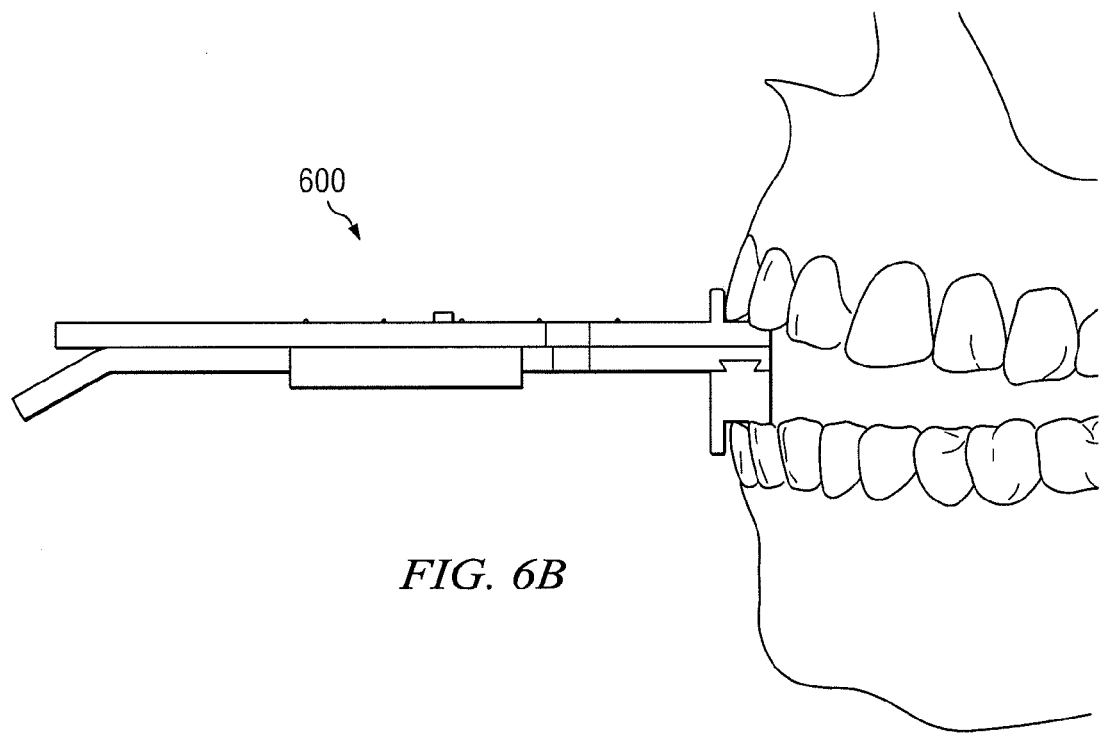
FIG. 6B illustrates an alternative view of an example embodiment of the system illustrated in FIG. 6 as positioned on maxillary dentition and mandibular dentition.
Figure 6C:
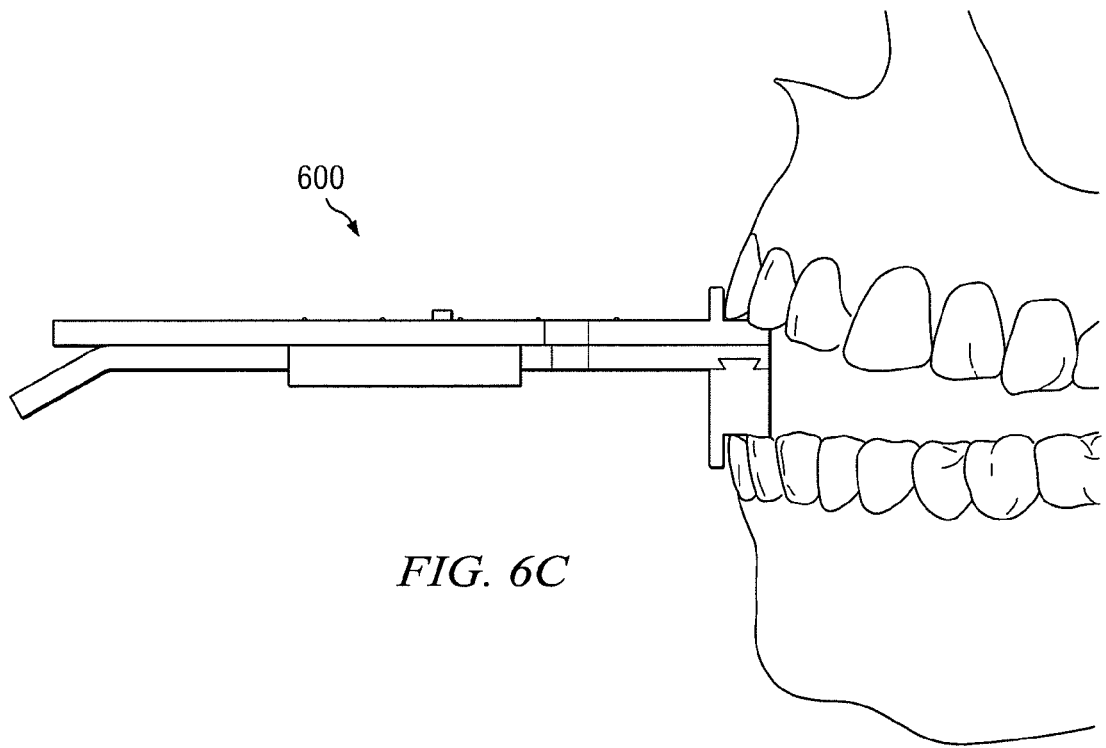
FIG. 6C illustrates another alternative view of an example embodiment of the system illustrated in FIG. 6 as positioned on maxillary dentition and mandibular dentition.

FIGS. 6A-6C illustrate an example embodiment of system 600 illustrated in FIG. 6 as implemented on a user, with system 600 adjusted to measure mandibular position across different angles of mandibular opening. FIG. 6A illustrates an embodiment of system 600 as positioned on a user's maxillary and mandibular dentition with a minimum-height lower bite insert 618. FIG. 6B illustrates an embodiment of system 600 as positioned on a user's maxillary and mandibular dentition with a mid-height lower bite insert 618. FIG. 6C illustrates an embodiment of system 600 as positioned on a user's maxillary and mandibular dentition with a maximum-height lower bite insert 618.

Figure 7:
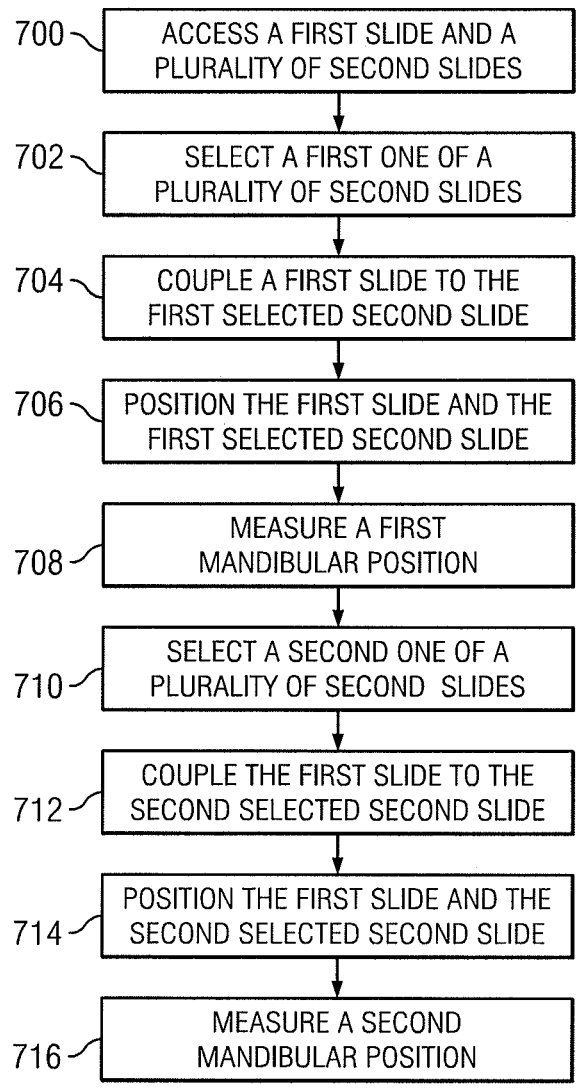
FIG. 7 is a flowchart illustrating methods of measuring mandibular position.

FIG. 7 is a flow chart illustrating an example operation of a particular embodiment of system 500 as illustrated in FIG. 5 in measuring the mandibular position.

At step 700, a first slide and a plurality of second slides are accessed. The slides may be accessed by a user, a medical practitioner or any other person. In particular embodiments, the first slide may be upper slide 502 and the plurality of second slides may be lower slides 504a, 504b, and 504c. In general however, the first slide and the plurality of second slides may be any appropriate number or type of slides suitable to perform the described functions.

At step 702, one of the plurality of second slides is selected. In particular embodiments, lower slide 504a is selected from among lower slide 504a, 504b, and 504c. As discussed above, system 500 may be used to measure a user's mandibular position across varying angles of mandibular opening. As a result, any one of a plurality of lower slides 504 may be selected to begin measuring a user's mandibular position. For purposes of this example, lower slide 504a is selected first. In other embodiments of system 500, lower slide 504b or lower slide 504c, or another lower slide 504 may be selected first.

At step 704, the selected one of the plurality of second slides is coupled to the first slide. In particular embodiments, lower slide 504a is coupled to upper slide 502. Lower slide 504a may be coupled to upper slide 502 by engaging lower slide 504a with upper guide 506. As discussed above, lower slide 504a may fit within a groove or slot of upper guide 506. Additionally, upper guide 506 may be appropriately sized so as to resist loose movement of lower slide 504a, yet guide the movement of lower slide 504a.

At step 706, the first slide and the selected one of the plurality of second slides are positioned on or adjacent to the dentition of a user. In particular embodiments, upper slide 502 and lower slide 504a are positioned on or adjacent to the user's dentition. Upper slide 502 and lower slide 504a may be positioned on or adjacent to the user's dentition by placing at least a portion of a user's maxillary dentition on upper bite portion 516 and a portion of a user's mandibular dentition on lower bite portion 518. In particular embodiments, upper bite portion 516 and lower bite portion 518 may include upper projections 508a and 508b and lower projections 510a and 510b, respectively. In such embodiments, a user's maxillary dentition may be placed in a gap between upper projections 508a and 508b, and a user's mandibular dentition may be placed in a gap between lower projections 510a and 510b.

At step 708, a first mandibular position is measured. In particular embodiments, the user's mandible may be extended in a forward or anterior direction. For example, in certain embodiments, a user may exert pressure on lower projections 510a and 510b by extending his or her mandible in an anterior direction. As force is applied, lower slide 504a moves within upper guide 506. In other embodiments, a practitioner may exert force on one of the upper slide 502 or lower slide 504a to extend the user's mandible in a forward or anterior position, or may manually extend the user's mandible itself. As lower slide 504a moves relative to upper slide 502, indicator 514 moves within a slot on the surface of upper slide 502. Once the mandible is extended in an anterior direction, the user's mandibular position may be measured. The mandibular position may be measured by noting a location of indicator 514 relative to measurement scale 522.

At step 710, a second one of the plurality of second slides is selected. In particular embodiments, lower slide 504b may be selected. As discussed above, in particular embodiments, multiple measurements of a user's mandibular position may be taken. Different lower slides 504 may be utilized for different angles of mandibular opening. In particular embodiments, bite portion 516 of lower slide 504b may be thicker than bite portion 516 of lower slide 504a in a direction orthogonal to a long axis of lower slide 504a and lower slide 504b. As a result, lower slide 504b may be used to measure the mandibular position with a wider mandibular opening.

At step 712, the second one of the plurality of second slides is coupled to the first slide. In particular embodiments, lower slide 504a may be decoupled from upper slide 502, and lower slide 504b may be coupled to upper slide 504c. As discussed above, lower slide 504b may couple to upper slide 502 by engaging with a groove or slot of upper guide 506. Additionally, upper guide 506 may be appropriately sized so as to resist loose movement of lower slide 504a, yet guide the movement of lower slide 504b.

At step 714, the second one of the plurality of second slides and the first slide are positioned on or adjacent to the user's dentition. In particular embodiments, upper slide 502 and lower slide 504b are positioned on or adjacent to the user's dentition by placing at least a portion of a user's maxillary dentition on upper bite portion 516 and a portion of a user's mandibular dentition on lower bite portion 518. As discussed above, lower bite portion 518 of lower slide 504b may be thicker in a direction orthogonal to a long axis of lower slide 504b than lower bite portion of lower slide 504a.

In step 716, a second mandibular position is measured. As discussed above, in particular embodiments, the user's mandible may be extended in a forward or anterior direction. As lower slide 504b moves, indicator 514 moves along the slot in upper slide 502. A second mandibular position may be measured by observing a location of indicator 514 relative to measurement scale 512.

In various embodiments, the steps illustrated in FIG. 7 may be combined, modified, or deleted where appropriate, and additional steps may also be added to those shown. Additionally, the steps may be performed in any suitable order without departing from the scope of operation of system 500. Additionally, although the process described above includes two measurements of a user's mandibular position being taken with lower slides 504a and 504b, the process may be repeated and/or supplemented with any appropriate number of measurements and/or any appropriate number and/or size of lower slides 504, including, but not limited to, lower slide 504c. Additionally, any number of measurements utilizing any appropriate heights of lower bite portions 518 may be taken, corresponding to the particular granularity of measurements desired.

Although the present disclosure has been described with several embodiments, numerous changes, variations, alterations, transformations, and modifications may be suggested to one skilled in the art, and it is intended that the present disclosure encompass such changes, variations, alterations, transformations, and modifications as fall within the scope of the appended claims.

What is claimed is:

1. An apparatus for measuring mandibular position comprising:
   a first slide operable to adjustably couple to a second slide, such that the second slide is operable to travel in a direction substantially parallel to a long axis of the first slide;
   an indicator configured to indicate a location of the second slide relative to the first slide in the direction substantially parallel to the long axis of the first slide; and
   an adjustment mechanism coupled to the first slide and the second slide, the adjustment mechanism configured to adjust the distance between the first slide and the second slide in a direction substantially orthogonal to the long axis of the first slide;
   wherein the first slide comprises a proximal end configured to be positioned proximate to the dentition of a user and an upper projection coupled to the proximal end of the upper slide, the upper projection extending from the first slide in a direction substantially orthogonal to the long axis of the first slide and configured to engage with at least a portion of a user's maxillary dentition; and
   wherein the second slide comprises a proximal end configured to be positioned proximate to the dentition of a user and a lower projection coupled to the proximal end of the slide, the lower projection extending in a direction substantially orthogonal to the long axis of the second slide and configured to engage with at least a portion of a user's mandibular dentition.

2. An apparatus for measuring mandibular position comprising:
   a middle slide comprising a tapered portion and a planar portion, wherein the middle slide is configured to adjustably couple to an upper slide and adjustably couple to a lower slide;
   the upper slide comprising a proximal end configured to be positioned proximate to the dentition of a user, a distal end configured to be positioned remote from the dentition of a user, a tapered portion configured to adjustably couple to the middle slide and to travel along the tapered portion of the middle slide, and an upper projection coupled to the proximal end of the upper slide, wherein the upper projection is configured to engage with at least a portion of a user's maxillary dentition;
   a lower slide comprising a proximal end configured to be positioned proximate to the dentition of the user, wherein the lower slide is configured to adjustably couple to the middle slide, and a lower projection coupled to the proximal end of the lower slide, wherein the lower projection is configured to engage with at least a portion of the user's mandibular dentition;
   an indicator configured to indicate a location of the lower slide relative to the upper slide in a direction substantially parallel to a long axis of the first slide; and
   an adjustment mechanism operable to adjust a distance between the upper slide and the lower slide in a direction substantially orthogonal to the long axis of the upper slide.

3. The apparatus of claim 2, wherein the upper projection is configured to engage with at least a portion of a user's maxillary dentition by being positioned adjacent to a portion of the user's maxillary dentition, and wherein the lower projection is operable to engage with at least a portion of a user's mandibular dentition by being positioned adjacent to a portion of the user's mandibular dentition.

4. The apparatus of claim 2, wherein the middle slide further comprises:
   a proximal end configured to be positioned proximate to the dentition of a user; and
   a distal end configured to be positioned remote from the dentition of a user;
   wherein the adjustment mechanism is further configured to pivotally couple to the proximal end of the middle slide and to pivotally couple to the distal end of the upper slide; and
   wherein the adjustment mechanism is disposed within at least a portion of the upper slide and within at least a portion of the middle slide.

5. The apparatus of claim 2, wherein the adjustment mechanism is configured to adjust a distance between the upper slide and the lower slide by moving the tapered portion of the middle slide along the tapered portion of the upper slide.

6. The apparatus of claim 2, wherein the upper slide further comprises a plurality of measurement marks, wherein the plurality of measurement marks is disposed along the long axis of the upper slide.

7. The apparatus of claim 6, wherein the indicator is further configured to couple to the lower slide and extend along a side portion of the upper slide proximate to the plurality of measurement marks.

8. The apparatus of claim 2, wherein the upper slide further comprises a guide disposed on the tapered portion of the upper slide, and wherein the upper slide is configured to adjustably couple to the middle slide by engaging the middle slide with one or more grooves in the guide.

9. The apparatus of claim 2, wherein the middle slide further comprises a guide, and wherein the middle slide is configured to adjustably couple to the lower slide by engaging the lower slide with one or more grooves in the guide.

10. The apparatus of claim 2, wherein the lower slide is further configured to travel in a direction substantially parallel to a long axis of the upper slide.

11. A system for measuring mandibular position comprising:
    a first slide comprising a first bite surface;
    a second slide configured to adjustably couple to the first slide;
    an indicator operable to indicate a location of the second slide relative to the first slide in a direction substantially parallel to a long axis of the first slide; and
    a plurality of inserts, each comprising a second bite surface, wherein each of the plurality of inserts is configured to couple to the second slide such that when the second slide is coupled to the first slide, the first bite surface and the second bite surface face substantially opposing directions orthogonal to the long axis of the first slide, wherein each of the inserts has a projection height in a direction orthogonal to the long axis of the first slide, and wherein the projection height is different for each of the plurality of inserts.

12. The system of claim 11, wherein the second slide comprises a proximal end configured to be positioned proximate to the dentition of a user, and wherein each of the plurality of inserts is configured to:
    removably couple to the proximal end of the second slide; and
    engage with at least a portion of the mandibular dentition of the user.

13. The system of claim 12, wherein each of the plurality of inserts is configured to engage with at least a portion of the mandibular dentition of the user by being positioned adjacent to the portion of the mandibular dentition of the user.

14. The system of claim 11, wherein the first slide comprises:
   a slot positioned along a long axis of the first slide; and
   a plurality of measurement marks, wherein each of the measurement marks is positioned along the slot.

15. The system of claim 14, wherein the indicator is further configured to:
   couple to at least one of the first slide and the second slide; and
   extend along a side portion of the first slide proximate to the plurality of measurement marks.

16. The system of claim 11, wherein the first slide comprises a guide, and wherein the first slide is configured to adjustably couple to the second slide by engaging the second slide with the guide.

17. The system of claim 11, wherein the second slide is further operable to travel in a direction substantially parallel to a long axis of the first slide.

18. A system for measuring mandibular position comprising:
   a first slide comprising a proximal end configured to be positioned proximate to the dentition of a user;
   a plurality of second slides, wherein each of the second slides is configured to removably couple to the first slide and to travel in a direction substantially parallel to a long axis of the first slide, wherein each of the plurality of second slides comprises a bite portion configured to be positioned proximate to the dentition of the user, wherein each of the bite portions comprises a bite portion height in a direction orthogonal to a long axis of the second slide, and wherein the bite portion height is different for each of the plurality of second slides; and
   an indicator configured to indicate a location of one of the plurality of second slides relative to the first slide in a direction substantially parallel to the long axis of the first slide.

19. The system of claim 18, further comprising:
   a first projection coupled to a proximal end of the first slide, wherein the first projection is configured to engage with at least a portion of the maxillary dentition of a user; and
   a plurality of second projections, wherein each of the plurality of second projections is coupled to the bite portion of one of the plurality of second slides, and wherein each of the plurality of second projections is configured to engage with at least a portion of the mandibular dentition of the user.

20. The system of claim 18, further comprising:
   a slot disposed in parallel along the long axis of the first slide; and
   a plurality of measurement marks, wherein each of the measurement marks is positioned along the slot.

21. The system of claim 20, further comprising a plurality of indicators, each of the plurality of indicators coupled to one of the plurality of second slides, and wherein each of plurality of indicators is configured to be positioned within the slot and to indicate, on the plurality of measurement marks, a location of the second slide relative to the first slide in a direction substantially parallel to the long axis of the first slide.

22. The system of claim 18, wherein the first slide comprises a guide, and wherein the first slide is configured to removably couple to each of the plurality of second slides by alternately engaging each of the plurality of second slides with one or more grooves in the guide.

23. The system of claim 18, wherein each of the plurality of second slides is further operable to travel in a direction substantially parallel to a long axis of the first slide.

24. A method for measuring mandibular position using a first slide and at least one of a plurality of second slides, the method comprising:
   selecting one of the plurality of second slides;
   coupling the first slide to the selected one of the plurality of second slides, such that a long axis of the first slide is substantially parallel with a long axis of the selected one of the plurality of second slides;
   engaging at least a portion of the maxillary dentition of a user and at least a portion of the mandibular dentition of the user with the first slide and the selected one of the plurality of second slides, such that the long axis of the first slide and the long axis of the selected one of the plurality of second slides are oriented substantially in the anterior-posterior direction with respect to the user's dentition; and
   measuring, using the first slide and the selected one of the plurality of second slides, a first position of the user's mandibular dentition relative to the user's maxillary dentition in the anterior-posterior direction.

25. The method of claim 24, further comprising:
   selecting a second one of the plurality of second slides;
   coupling the first slide to the selected second one of the plurality of second slides;
   engaging at least a portion of the maxillary dentition of the user and at least a portion of the mandibular dentition of the user with the first slide and the selected one of the plurality of second slides, such that the long axis of the first slide and the long axis of the selected second one of the plurality of second slides are oriented substantially in the anterior-posterior direction with respect to the user's dentition; and
   measuring, using the first slide and the selected second one of the plurality of second slides, a second position of the user's mandibular dentition relative to the user's maxillary dentition in the anterior-posterior direction.

26. A method for measuring mandibular position using a first slide and at least one of a plurality of second slides, the method comprising:
   selecting one of the plurality of second slides;
   coupling the first slide to the selected one of the plurality of second slides;
   engaging at least a portion of the maxillary dentition of a user and at least a portion of the mandibular dentition of the user with the first slide and the selected one of the plurality of second slides; and
   measuring a first mandibular position,
   wherein each of the plurality of second slides comprises a bite portion configured to be positioned proximate to the dentition of the user, wherein each of the bite portions comprises a bite portion height in a direction orthogonal to a long axis of the second slide, and wherein the bite portion height is different for each of the plurality of second slides.

27. The method of claim 26, wherein engaging at least a portion of the maxillary dentition of the user and at least a portion of the mandibular dentition of the user with the first slide and the selected one of the plurality of second slides comprises positioning a first projection adjacent to a portion of the maxillary dentition of the user, wherein the first projection is coupled to a proximal end of the first slide, and positioning a second projection adjacent to a portion of the mandibular dentition of the user, wherein the second projection is coupled to the bite portion of the selected one of the plurality of second slides.

28. The method of claim 24, wherein the first slide comprises:
- a slot disposed in parallel along a long axis of the first slide; and
- a plurality of measurement marks, wherein each of measurement marks is positioned along the slot.

29. The method of claim 28, wherein each of the plurality of second slides comprises an indicator, and wherein measuring a first mandibular position comprises determining a location of the indicator of the selected one of the plurality of second slides relative to the plurality of measurement marks.

30. The method of claim 24, wherein the first slide comprises a guide, and wherein coupling the first slide to the selected one of the plurality of second slides comprises engaging the selected one of the plurality of second slides with one or more grooves in the guide.

31. The method of claim 24, wherein the selected one of the plurality of second slides is operable to travel in a direction substantially parallel to the long axis of the first slide.

\* \* \* \* \*